United States Patent
Cui et al.

(10) Patent No.: US 9,896,519 B2
(45) Date of Patent: Feb. 20, 2018

(54) METALLOCENE COMPLEX, PREPARATION METHOD THEREOF AND CATALYST COMPOSITION

(71) Applicant: Changchun Institute of Applied Chemistry Chinese Academy of Sciences, Changchun, Jilin (CN)

(72) Inventors: Dongmei Cui, Jilin (CN); Chunji Wu, Jilin (CN); Changguang Yao, Jilin (CN)

(73) Assignee: Changchun Institute of Applied Chemistry Chinese Academy of Sciences, Changchun, Jilin (CN)

( * ) Notice: Subject to any disclaimer, the term of this patent is extended or adjusted under 35 U.S.C. 154(b) by 0 days.

(21) Appl. No.: 15/025,244

(22) PCT Filed: Nov. 11, 2013

(86) PCT No.: PCT/CN2013/086850
§ 371 (c)(1),
(2) Date: Mar. 25, 2016

(87) PCT Pub. No.: WO2015/051569
PCT Pub. Date: Apr. 16, 2015

(65) Prior Publication Data
US 2016/0229928 A1    Aug. 11, 2016

(30) Foreign Application Priority Data

Oct. 12, 2013    (CN) .......................... 2013 1 0478190

(51) Int. Cl.
*C08F 4/52* (2006.01)
*C08F 10/00* (2006.01)
(Continued)

(52) U.S. Cl.
CPC ................... *C08F 4/58* (2013.01); *C07F 5/00* (2013.01); *C07F 17/00* (2013.01); *C07F 19/00* (2013.01);
(Continued)

(58) Field of Classification Search
CPC .. C08F 4/52; C08F 10/00; C08F 10/02; C08F 36/20; C08F 12/08
See application file for complete search history.

(56) References Cited

U.S. PATENT DOCUMENTS 6,444,833 B1 *  9/2002  Ewen .................... C07D 333/78
                                                          502/103
7,238,818 B2 *  7/2007  Ewen .................... C07D 333/70
                                                          502/103
(Continued)

FOREIGN PATENT DOCUMENTS

CN        101010349      8/2007
CN        101442243      5/2009
WO    WO 2015/051569     4/2015

OTHER PUBLICATIONS

Luo et al., "Scandium Half-Metallocene-Catalyzed Syndiospecific Styrene Polymerization and Styrene-Ethylene Copolymerization: Unprecedented Incorporation of Syndiotactic Styrene-Styrene Sequences in Stryene-Ethylene Copolymers", J. Am. Chem. Soc., 126:13910-13911 (Oct. 12, 2004).
(Continued)

*Primary Examiner* — Caixa Lu
(74) *Attorney, Agent, or Firm* — Knobbe, Martens, Olson & Bear, LLP

(57) ABSTRACT

This invention provides a metallocene complex and the preparation method thereof and a catalyst composition. This catalyst composition comprises a metallocene complex represented by formula (I) and an organic boron salt. Compared to the prior art, the catalyst used in this invention, which is the metallocene complex represented by formula (I), does not contain a group bonding between the heterocyclic fused cyclopentadienyl ring and the transition metal, and the coordination space of the central metal has a large opening degree. Therefore, the catalytic activity for more sterically hindered monomers is higher, and the comonomer incorporation is also higher. Furthermore, the metallocene complex represented by formula (I) used in this invention is a heterocyclic ring fused cyclopentadienyl ligand. Heterocyclic rings have relatively strong electron-donating capacity. By fusing a cyclopentadienyl group using heterocyclic rings, it is possible to change the electronic effect of the metal center and in turn increase the activity of catalyst. Therefore, by using the metallocene complex represented by formula (I), it is possible to prepare copolymers of ethylene with other olefins at high activity and high comonomer incorporation, and it is also possible to catalyze the polymerization of styrene and substituted styrene at high syndiotacticity and high activity.

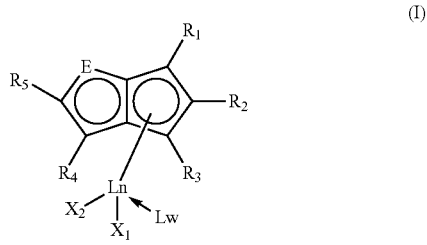

10 Claims, 3 Drawing Sheets

(51) Int. Cl.
*C08F 36/20* (2006.01)
*C08F 12/08* (2006.01)
*C08F 4/58* (2006.01)
*C07F 19/00* (2006.01)
*C07F 17/00* (2006.01)
*C07F 5/00* (2006.01)

(52) U.S. Cl.
CPC ............... *C08F 4/52* (2013.01); *C08F 10/00* (2013.01); *C08F 12/08* (2013.01); *C08F 36/20* (2013.01); *C08F 2420/06* (2013.01)

(56) References Cited

U.S. PATENT DOCUMENTS

| | | | |
|---|---|---|---|
| 7,994,267 B2* | 8/2011 | Hou | ................. C08F 10/00 526/134 |
| 8,653,290 B2* | 2/2014 | Kaita | ................. C07F 17/00 502/155 |

OTHER PUBLICATIONS

Naga, "Copolymerization of Ethylene with Cycloolefins or Cyclodiolefins by a Constrained-Geometry Catalyst", Journal of Polymer Science: Part A: Polymer Chemistry, 43:1285-1291 (2005).
Hultzsch et al., "Half-Sandwich Alkyl and Hydrido Complexes of Yttrium: Convenient Synthesis and Polymerization Catalysis of Polar Monomers**", Angew. Chem. Int. Ed. 38(1/2):227-230 (1999).
International Search Report and Written Opinion issued in application No. PCT/CN2013/086850 dated Jul. 18, 2014.

* cited by examiner

Chemical Shift (ppm)

Chemical Shift (ppm)

Chemical Shift (ppm)

METALLOCENE COMPLEX, PREPARATION METHOD THEREOF AND CATALYST COMPOSITION

FIELD OF THE INVENTION

This invention belongs to the technical field of catalysts, particularly to a metallocene complex, the preparation method thereof, and a catalyst composition.

BACKGROUND OF THE INVENTION

A metallocene complex refers to a compound wherein a central metal coordinates to one or more cyclopentadienyl groups or derivatives thereof, and plays a very important role in various polymerization reactions as a catalyst. Here, a metal complex in combination with one cyclopentadienyl group or one derivative becomes a mono-metallocene complex. As a result of different types of central metals, metallocene complexes have completely different properties, such as catalyst activities for polymerization reaction. Particularly, after organic borane $B(C_6F_5)_3$ and organic boron salts $[Ph_3C][B(C_6F_5)_4]$ and $[PhNMe_2H][B(C_6F_5)_4]$ are successfully prepared and are used as efficient activating agents, mono-metallocene rare earth organic complexes exhibit superior activity and selectivity of polymerization in terms of catalysis of polymerization of polar and non-polar monomers (such as conjugated dienes, styrene, ethylene, α-olefins, or the like).

Metallocene complexes containing Group III metals or lanthanide metals have been reported as follows. In 1999, a mono-yttrocene dialkyl complex $(C_5Me_4SiMe_2R)Y(CH_2SiMe_3)_2(THF)$ reported by German scientists, the group of Okuda, was milestone breakthrough (K. C. Hultzsch, T. P. Spaniol and J. Okuda, Angew. Chem. Int. Ed, 1999, 38, 227), and it exhibited high activity of olefin polymerization for the first time. The study group of Hou in Japan used a kind of mono-metallocene dialkyl rare earth metal complexes $(C_5Me_4SiMe_3)Sc(CH_2SiMe_3)_2(THF)$, which may induce high-syndiotactic selective polymerization of styrene and high-active and high-stereoselective copolymerization of ethylene with styrene under the activation of an organic boron salt $[Ph_3C][B(C_6F_5)_4]$ (Y. Luo, J. Baldamus and Z. Hou, *J. Am. Chem. Soc.*, 2004, 126, 13910; US2007/0232758A1), and recently they successfully achieved binary copolymerization of styrene with 1,6-heptadiene or 1,5-hexadiene, ternary copolymerization of styrene and ethylene with 1,6-heptadiene or 1,5-hexadiene, and copolymerization of a cycloalkene (DCPD, norbornene) with 1-hexene by using a catalytic system of a benzylalkyl complex $(C_5Me_4SiMe_3)Sc(CH_2C_6H_4NMe_2\text{-}o)_2/[Ph_3C][B(C_6F_5)_4]$ (F. Guo, M. Nishiura, H. Koshino and Z. Hou, *Macromolecules* 2011, 44, 2400; F. Guo, M. Nishiura, H. Koshino and Z. Hou, *Macromolecules* 2011, 44, 6335).

Cycloalkene polymers are expected to be used in optical materials instead of PMMA and PC due to their excellent heat resistance, strength, and optical properties. The major part in the petroleum cracking product C5-fraction is cyclopentadiene, which may spontaneously undergo Diels-Alder reaction at room temperature to be converted to DCPD. Therefore, the studies on copolymerization reactions of DCPD with ethylene, α-olefins, or styrene have been widely focused on. In recent years, with respect to catalysts for polymerization of ethylene with DCPD, ones which have been much studied are Ti and Zr complexes. However, DCPD has two active double bonds, wherein the activity of the carbon double bond at 5 and 6 positions is higher the carbon double bond at 2 and 3 positions, and when a copolymerization reaction of DCPD with an ethylene type monomer is performed using Ti and Zr polymerization catalysts, a crosslinked polymer is easily available (Naga, N. *J. Polym. Sci., Part A: Polym. Chem.* 2005, 43, 1285-1291) or the molecular weight of the copolymer and the content of DCPD are both relatively low. Transition metal compounds having heterocyclic ring fused 5-membered ring π ligands and olefin polymerization reaction using these transition metal compounds have been studied, and their catalytic advantages are high activity, high molecular weight, and so on. However, these transition metal complexes all contain side chains, mono-metallocene complexes without side chains having larger opening space have not been reported yet.

SUMMARY OF THE INVENTION

In view of this, the technical problem to be solved by this invention is to provide a metallocene complex, its preparation method and a catalyst composition, wherein the metallocene complex does not contain a group bonding between the heterocyclic fused cyclopentadienyl ring and the transition metal.

This invention provides a metallocene complex represented by formula (I):

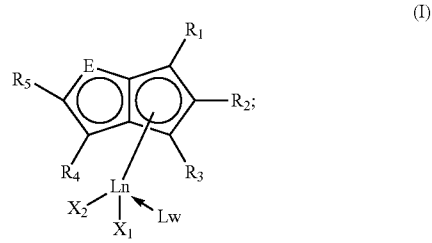

wherein Ln is one of scandium (Sc), yttrium (Y) and the fifteen elements of lanthanides having an atomic number of 57-71;

$R_1$, $R_2$, $R_3$, $R_4$, and $R_5$ are each independently selected from one of H, a C1-C20 alkyl group, a C1-C20 alkyl group containing an acetal group, a C1-C20 alkyl group containing a ketal group, a C1-C20 alkyl group containing an ether group, a C1-C20 alkenyl group, a C1-C20 alkenyl group containing an acetal group, a C1-C20 alkenyl group containing a ketal group, a C1-C20 alkenyl group containing an ether group, a C6-C20 aryl group, a C6-C20 aryl group containing an acetal group, a C6-C20 aryl group containing a ketal group, a C6-C20 aryl group containing an ether group, a C1-C20 silyl group, a C1-C20 silyl group containing an acetal group, a C1-C20 silyl group containing a ketal group, and a C1-C20 silyl group containing an ether group, or $R_1$ and $R_2$ are linked to each other to form a ring, or $R_2$ and $R_3$ are linked to each other to form a ring, or $R_4$ and $R_5$ are linked to each other to form a ring;

E is O, S or N—R; said R is a methyl group, a benzene ring, or a substituted benzene ring;

$X_1$ and $X_2$ are each independently selected from one of hydrogen, a C1-C20 aliphatic group, a C1-C20 alicyclic group, a phenyl group, a substituted phenyl group, a C1-C20 alkoxy group, a C1-C20 alkylamino group, a C1-C20 arylamino group, a C1-C20 silyl group, an allyl group, an allyl derivative, a borohydride group, and a halogen atom; said substituted phenyl group is a phenyl group substituted by one or more of a C1-C20 aliphatic group, a C1-C20 alicyclic group, and an aromatic group;

L is a neutral Lewis base, and w is an integer of 0-3.

Preferably, said C1-C20 aliphatic group is selected from one of a methyl group, an ethyl group, a propyl group, an isopropyl group, a butyl group, a sec-butyl group, and a tert-butyl group.

Preferably, said $X_1$ and $X_2$ are each independently selected from one of a silylamino group, a dimethylamino group, a diethylamino group, a dipropylamino group, a N,N-dimethylaminophenyl group, a (trimethylsilyl)methyl group, a bis(trimethylsilyl)methyl group, an o-methylthiophenyl group, an o-dimethylphosphinophenyl group, a tetrahydroboryl group, a methoxy group, an ethoxy group, an isopropoxy group, a n-propoxy group, and a n-butoxy group.

Preferably, said allyl derivative is —$C_3H_nR_6$; said n is 3 or 4; said $R_6$ is a C1-C20 aliphatic group, a C1-C20 alicyclic group, a phenyl group, or a substituted phenyl group; said substituted phenyl group is a phenyl group substituted by one or more of a C1-C20 aliphatic group, a C1-C20 alicyclic group, and an aromatic group.

Preferably, said L is tetrahydrofuran, ethyl ether, or toluene.

This invention further provides a preparation method of a metallocene complex, comprising:

performing a reaction of a cyclopentadienyl ligand represented by formula (II) and a rare earth compound in a first organic solvent under the protective condition of an inert gas to obtain a metallocene complex represented by formula (I), wherein $X_1$ and $X_2$ are each independently a C1-C20 silyl group; said rare earth compound contains groups $X_1$ and $X_2$;

or, performing a first reaction of a cyclopentadienyl ligand represented by formula (II) and an alkyl lithium in a second organic solvent under the protective condition of an inert gas, then performing a second reaction by adding a rare earth halide, and performing a third reaction by further adding an allyl Grignard reagent and/or an allyl derivative Grignard reagent, to obtain a metallocene complex represented by formula (I) wherein $X_1$ and $X_2$ are each independently an allyl group or an allyl derivative;

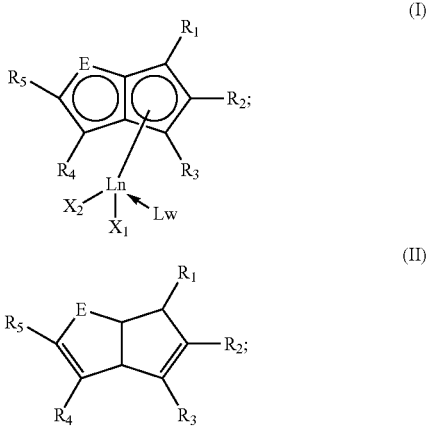

wherein Ln is one of scandium (Sc), yttrium (Y) and the fifteen elements of lanthanides having an atomic number of 57-71;

$R_1$, $R_2$, $R_3$, $R_4$, and $R_5$ are each independently selected from one of H, a C1-C20 alkyl group, a C1-C20 alkyl group containing an acetal group, a C1-C20 alkyl group containing a ketal group, a C1-C20 alkyl group containing an ether group, a C1-C20 alkenyl group, a C1-C20 alkenyl group containing an acetal group, a C1-C20 alkenyl group containing a ketal group, a C1-C20 alkenyl group containing an ether group, a C6-C20 aryl group, a C6-C20 aryl group containing an acetal group, a C6-C20 aryl group containing a ketal group, a C6-C20 aryl group containing an ether group, a C1-C20 silyl group, a C1-C20 silyl group containing an acetal group, a C1-C20 silyl group containing a ketal group, and a C1-C20 silyl group containing an ether group, or $R_1$ and $R_2$ are linked to each other to form a ring, or $R_2$ and $R_3$ are linked to each other to form a ring, or $R_4$ and $R_5$ are linked to each other to form a ring;

E is O, S or N—R; said R is a methyl group, a benzene ring, or a substituted benzene ring;

$X_1$ and $X_2$ are each independently selected from one of a C1-C20 silyl group, an allyl group, and an allyl derivative;

L is a neutral Lewis base, and w is an integer of 0-3.

This invention further provides a catalyst composition, comprising a metallocene complex represented by formula (I) and an organic boron salt;

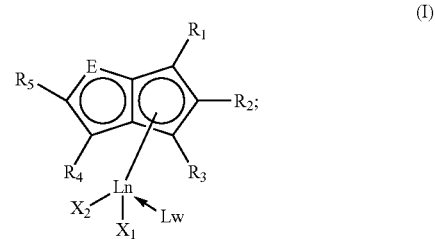

wherein Ln is one of scandium (Sc), yttrium (Y) and the fifteen elements of lanthanides having an atomic number of 57-71;

$R_1$, $R_2$, $R_3$, $R_4$, and $R_5$ are each independently selected from one of H, a C1-C20 alkyl group, a C1-C20 alkyl group containing an acetal group, a C1-C20 alkyl group containing a ketal group, a C1-C20 alkyl group containing an ether group, a C1-C20 alkenyl group, a C1-C20 alkenyl group containing an acetal group, a C1-C20 alkenyl group containing a ketal group, a C1-C20 alkenyl group containing an ether group, a C6-C20 aryl group, a C6-C20 aryl group containing an acetal group, a C6-C20 aryl group containing a ketal group, a C6-C20 aryl group containing an ether group, a C1-C20 silyl group, a C1-C20 silyl group containing an acetal group, a C1-C20 silyl group containing a ketal group, and a C1-C20 silyl group containing an ether group, or $R_1$ and $R_2$ are linked to each other to form a ring, or $R_2$ and $R_3$ are linked to each other to form a ring, or $R_4$ and $R_5$ are linked to each other to form a ring;

E is O, S or N—R; said R is a methyl group, a benzene ring, or a substituted benzene ring;

$X_1$ and $X_2$ are each independently selected from one of hydrogen, a C1-C20 aliphatic group, a C1-C20 alicyclic group, a phenyl group, a substituted phenyl group, a C1-C20 alkoxy group, a C1-C20 alkylamino group, a C1-C20 arylamino group, a C1-C20 silyl group, an allyl group, an allyl derivative, a borohydride group, and a halogen atom; said substituted phenyl group is a phenyl group substituted by one or more of a C1-C20 aliphatic group, a C1-C20 alicyclic group, and an aromatic group;

L is a neutral Lewis base, and w is an integer of 0-3.

Preferably, an alkyl aluminum is further comprised.

This invention further provides a preparation method of a polymer, comprising:

mixing the catalyst composition with an olefin monomer and performing a polymerization reaction to obtain the polymer.

Preferably, said olefin monomer is selected from one or more of styrene, substituted styrene, ethylene, α-olefin, cyclic olefin, and non-conjugated dienes.

This invention provides a metallocene complex and the preparation method thereof and a catalyst composition. This catalyst composition comprises a metallocene complex represented by formula (I) and an organic boron salt. Compared to the prior art, the catalyst used in this invention, which is the metallocene complex represented by formula (I), does not contain any side chain, and the coordination space of the central metal has a large opening degree. Therefore, the catalytic activity for more sterically hindered monomers is higher, and the comonomer incorporation is also higher. Furthermore, the metallocene complex represented by formula (I) used in this invention is a heterocyclic ring fused cyclopentadienyl ligand. Heterocyclic rings have relatively strong electron-donating capacity. By fusing a cyclopentadienyl group using heterocyclic rings, it is possible to change the electronic effect of the metal center and in turn increase the activity of catalyst. Therefore, by using the metallocene complex represented by formula (I), it is possible to prepare copolymers of ethylene with other olefins at high activity and high comonomer incorporation, and it is also possible to catalyze the polymerization of styrene and substituted styrene at high syndiotacticity and high activity.

DETAILED DESCRIPTION OF THE PREFERRED EMBODIMENT

Figure 1:
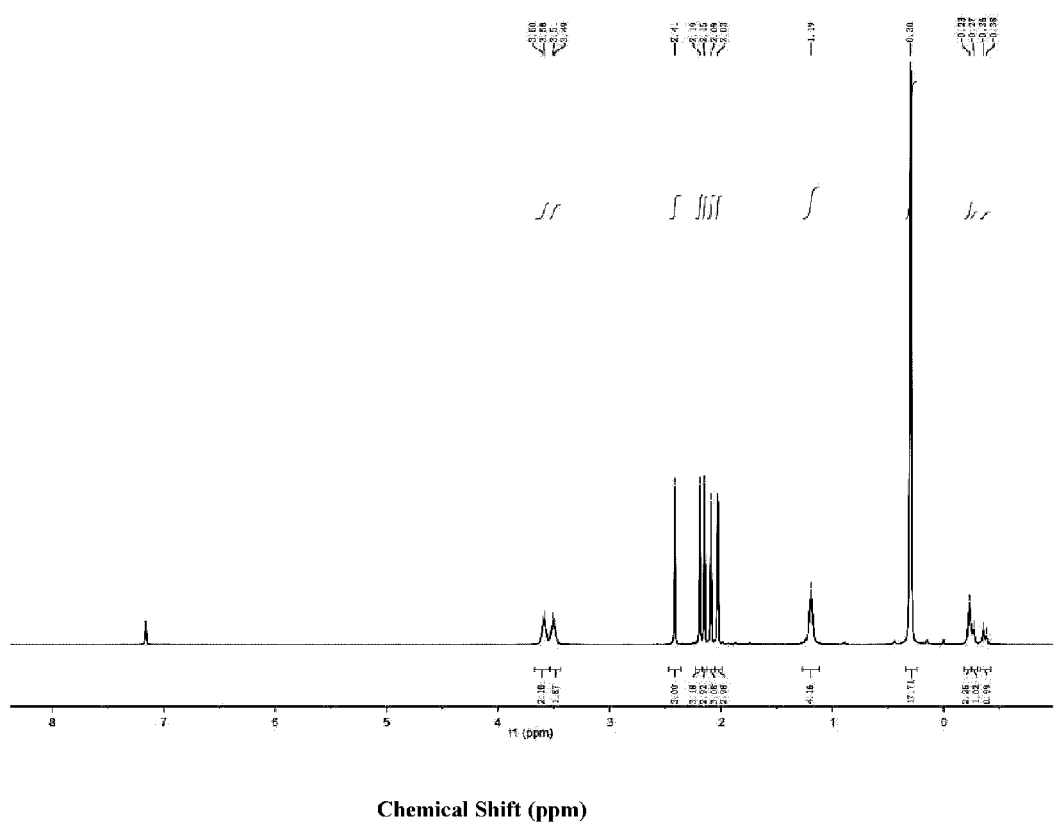
FIG. 1 is a hydrogen nuclear magnetic resonance spectrogram of a metallocene type scandium alkyl complex (I-2) obtained in Example 2 of this invention.

This invention provides a metallocene complex represented by formula (I):

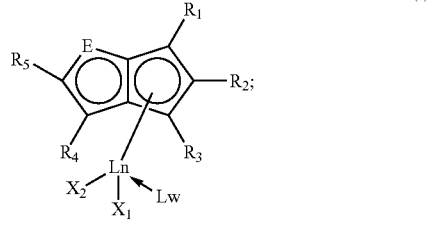

(I)

wherein Ln is one of scandium (Sc), yttrium (Y) and the fifteen elements of lanthanides having an atomic number of 57-71;

$R_1$, $R_2$, $R_3$, $R_4$, and $R_5$ are each independently selected from one of H, a C1-C20 alkyl group, a C1-C20 alkyl group containing an acetal group, a C1-C20 alkyl group containing a ketal group, a C1-C20 alkyl group containing an ether group, a C1-C20 alkenyl group, a C1-C20 alkenyl group containing an acetal group, a C1-C20 alkenyl group containing a ketal group, a C1-C20 alkenyl group containing an ether group, a C6-C20 aryl group, a C6-C20 aryl group containing an acetal group, a C6-C20 aryl group containing a ketal group, a C6-C20 aryl group containing an ether group, a C1-C20 silyl group, a C1-C20 silyl group containing an acetal group, a C1-C20 silyl group containing a ketal group, and a C1-C20 silyl group containing an ether group, or $R_1$ and $R_2$ are linked to each other to form a ring, or $R_2$ and $R_3$ are linked to each other to form a ring, or $R_4$ and $R_5$ are linked to each other to form a ring;

E is O, S or N—R; said R is a methyl group, a benzene ring, or a substituted benzene ring;

$X_1$ and $X_2$ are each independently selected from one of hydrogen, a C1-C20 aliphatic group, a C1-C20 alicyclic group, a phenyl group, a substituted phenyl group, a C1-C20 alkoxy group, a C1-C20 alkylamino group, a C1-C20 arylamino group, a C1-C20 silyl group, an allyl group, an allyl derivative, a borohydride group, and a halogen atom; said substituted phenyl group is a phenyl group substituted by one or more of a C1-C20 aliphatic group, a C1-C20 alicyclic group, and an aromatic group;

L is a neutral Lewis base, and w is an integer of 0-3.

According to this invention, Ln is one of scandium (Sc), yttrium (Y), and the fifteen elements of lanthanides having an atomic number of 57-71, and is preferably Sc, Y, La, Ce, Pr, Nd, Pm, Sm, Eu, Gd, Tb, Dy, Ho, Er, Tm, Yb, or Lu, more preferably Sc, Y, Lu, Dy, Er, or Gd.

$R_1$, $R_2$, $R_3$, $R_4$, and $R_5$ are each independently selected from one of H, a C1-C20 alkyl group, a C1-C20 alkyl group containing an acetal group, a C1-C20 alkyl group containing a ketal group, a C1-C20 alkyl group containing an ether group, a C1-C20 alkenyl group, a C1-C20 alkenyl group containing an acetal group, a C1-C20 alkenyl group containing a ketal group, a C1-C20 alkenyl group containing an ether group, a C6-C20 aryl group, a C6-C20 aryl group containing an acetal group, a C6-C20 aryl group containing a ketal group, a C6-C20 aryl group containing an ether group, a C1-C20 silyl group, a C1-C20 silyl group containing an acetal group, a C1-C20 silyl group containing a ketal group, and a C1-C20 silyl group containing an ether group; preferably, one of H, a C1-C10 alkyl group, a C1-C10 alkyl group containing an acetal group, a C1-C10 alkyl group containing a ketal group, a C1-C10 alkyl group containing an ether group, a C1-C10 alkenyl group, a C1-C10 alkenyl group containing an acetal group, a C1-C10 alkenyl group containing a ketal group, a C1-C10 alkenyl group containing an ether group, a C6-C18 aryl group, a C6-C28 aryl group containing an acetal group, a C6-C28 aryl group containing a ketal group, a C6-C28 aryl group containing an ether group, a C1-C10 silyl group, a C1-C10 silyl group containing an acetal group, a C1-C10 silyl group containing a ketal group, and a C1-C10 silyl group containing an ether group; and more preferably, one of H, a C1-C10 alkyl group, a C1-C10 alkenyl group, a silyl group, a phenyl group, a 2,6-dimethylphenyl group, a 2,6-diethylphenyl group, a 2,6-diisopropylphenyl group, and a 2,6-di-tert-butylphenyl group.

Or, $R_1$ and $R_2$ are linked to each other to form a ring, preferably linked to each other to form a 5-membered ring or a 6-membered ring; or, $R_2$ and $R_3$ are linked to each other to form a ring, preferably linked to each other to form a 5-membered ring or a 6-membered ring; or, $R_4$ and $R_5$ are linked to each other to form a ring, preferably linked to each other to form a 5-membered ring or a 6-membered ring; and when substituents may form a ring, the structure of the metallocene complex represented by formula (I) is as shown in the following formulae 1-4:

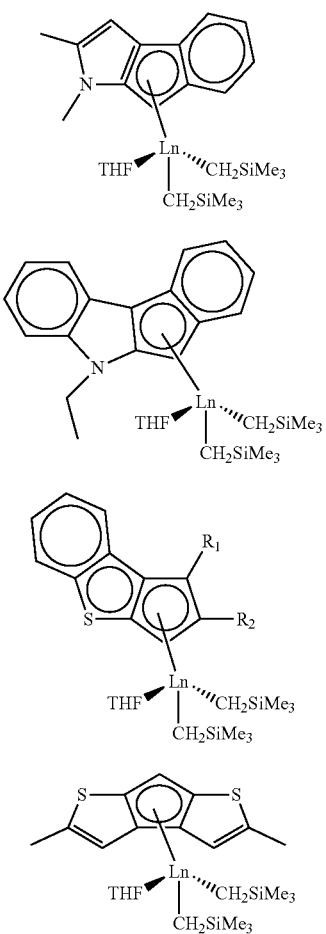

E is O, S or N—R; said R is a methyl group, a phenyl group, or a substituted phenyl group, preferably a methyl group or a phenyl group.

$X_1$ and $X_2$ are each independently selected from one of hydrogen, a C1-C20 aliphatic group, a C1-C20 alicyclic group, a phenyl group, a substituted phenyl group, a C1-C20 alkoxy group, a C1-C20 alkylamino group, a C1-C20 arylamino group, a C1-C20 silyl group, an allyl group, an allyl derivative, a borohydride group, and a halogen atom; said substituted phenyl group is a phenyl group substituted by one or more of a C1-C20 aliphatic group, a C1-C20 alicyclic group, and an aromatic group.

Here, said C1-C20 aliphatic group is preferably a C1-C10 aliphatic group, more preferably one of a methyl group, an ethyl group, a propyl group, an isopropyl group, a butyl group, and a sec-butyl group; said C1-C20 alicyclic group is preferably a C1-C10 alicyclic group, more preferably a C3-C6 alicyclic group; said C1-C20 alkoxy group is preferably a C1-C10 alkoxy group, more preferably a C1-05 alkoxy group, still more preferably one of a methoxy group, an ethoxy group, an isopropoxy group, a n-propoxy group, and a n-butoxy group; said C1-C20 alkylamino group is preferably a C1-C10 alkylamino group, more preferably one of a dimethylamino group, a diethylamino group, and a dipropylamino group; said C1-C20 arylamino group is preferably a C1-C10 arylamino group, more preferably a N,N-dimethylaminophenyl group; said C1-C20 silyl group is preferably a C1-C10 silyl group, more preferably a (trimethylsilyl)methyl group and a bis(trimethylsilyl)methyl group; said substituted phenyl group is preferably an o-methylthiophenyl group or an o-dimethylphosphinophenyl group; and said halogen is one of fluorine, chlorine, bromine, and iodine, and is not particularly limited.

Said allyl derivative is preferably —$C_3H_nR_6$; said n is 3 or 4; said $R_6$ is a C1-C20 aliphatic group, a C1-C20 alicyclic group, a phenyl group, or a substituted phenyl group; said substituted phenyl group is a phenyl group substituted by one or more of a C1-C20 aliphatic group, a C1-C20 alicyclic group, and an aromatic group. Here, the C1-C20 aliphatic group and the C1-C20 alicyclic group in said $R_6$ have the same range as those of the C1-C20 aliphatic group and the C1-C20 alicyclic group in the above said $X_1$ and $X_2$, and verbose words are omitted hereby.

According to this invention, preferably said $X_1$ and $X_2$ are each independently one of a silylamino group ($N(SiMe_3)_2$), a dimethylamino group, a diethylamino group, a dipropylamino group, a N,N-dimethylaminophenyl group, a (trimethylsilyl)methyl group, a bis(trimethylsilyl)methyl group, an o-methylthiophenyl group, an o-dimethylphosphinophenyl group, a tetrahydroboryl group, a methoxy group, an ethoxy group, an isopropoxy group, a n-propoxy group, a n-butoxy group, and an allyl group, more preferably a (trimethylsilyl)methyl group or an allyl group. Said $X_1$ and $X_2$ in this invention may be the same group or may also be different, and are not particularly limited.

L is a neutral Lewis base, w is an integer of 0-3. The neutral Lewis base is not particularly limited, as long as it is a neutral Lewis base well known by the person skilled in the art, and it is preferably tetrahydrofuran, ethyl ether, or toluene in this invention.

According to this invention, said metallocene complex represented by formula (I) is preferably a complex having one of the following structures:

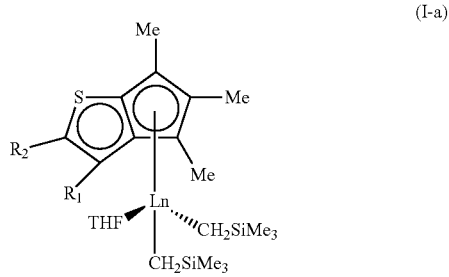

(I-a)

Ln = Sc $R_1$ = $R_2$ = H (complex 1)
$R_1$ = $R_2$ = Me (complex 2)
$R_1$ = H, $R_2$ = Me (complex 3)
Ln = Y $R_1$ = $R_2$ = H (complex 4)
$R_1$ = $R_2$ = Me (complex 5)
$R_1$ = H, $R_2$ = Me (complex 6)
Ln = Er $R_1$ = $R_2$ = H (complex 7)
$R_1$ = $R_2$ = Me (complex 8)
$R_1$ = H, $R_2$ = Me (complex 9)

(I-b)

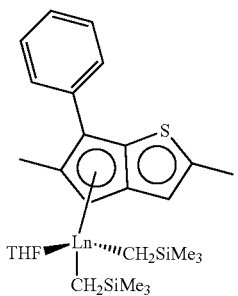

Ln = Sc (complex 10)
Ln = Y (compley 11)
Ln = Dy (complex 12)

(I-c)

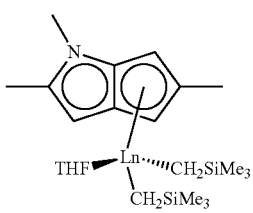

Ln = Sc (complex 13)
Ln = Y (complex 14)
Ln = Gd (complex 15)

(I-d)

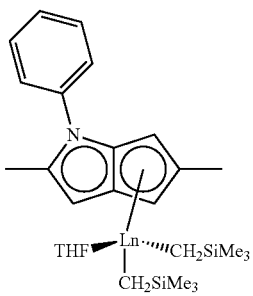

Ln = Sc (complex 16)
Ln = Y (complex 17)
Ln = Lu (complex 18)

(I-e)

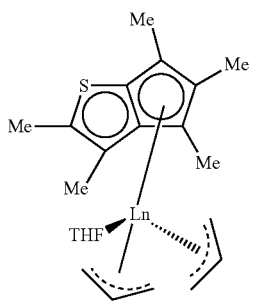

Ln = S (complex 19)
Ln = Y (complex 20)
Ln = Gd (complex 21)

(I-f)

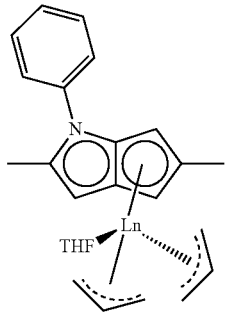

Ln = Sc (complex 22)
Ln = Y (complex 23)
Ln = Lu (complex 24)

The catalyst used in this invention, which is the metallocene complex represented by formula (I), does not contain any side chain, and the coordination space of the central metal has a large opening degree. Therefore, the catalytic activity for more sterically hindered monomers is higher, and the comonomer incorporation is also higher.

Furthermore, the metallocene complex represented by formula (I) used in this invention is a heterocyclic ring fused cyclopentadienyl ligand. Heterocyclic rings have relatively strong electron-donating capacity. By fusing a cyclopentadienyl group using heterocyclic rings, it is possible to change the electronic effect of the metal center and in turn increase the activity of catalyst. Therefore, by using the metallocene complex represented by formula (I), it is possible to prepare copolymers of ethylene with other olefins at high activity and high comonomer incorporation, and it is also possible to catalyze the polymerization of styrene and substituted styrene at high syndiotacticity and high activity.

This invention further provides a preparation method of the metallocene complex represented by formula (I) described above.

When $X_1$ and $X_2$ in the metallocene complex represented by formula (I) are each independently a C1-C20 alkoxy group, the metallocene complex represented by formula (I) is prepared according to the following step of: performing a reaction of a cyclopentadienyl ligand represented by formula (II) and a rare earth compound in a first organic solvent under the protective condition of an inert gas to obtain a metallocene complex represented by formula (I).

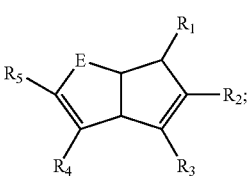

(II)

wherein Ln is one of scandium (Sc), yttrium (Y) and the fifteen elements of lanthanides having an atomic number of 57-71;

$R_1$, $R_2$, $R_3$, $R_4$, and $R_5$ are each independently selected from one of H, a C1-C20 alkyl group, a C1-C20 alkyl group containing an acetal group, a C1-C20 alkyl group containing a ketal group, a C1-C20 alkyl group containing an ether group, a C1-C20 alkenyl group, a C1-C20 alkenyl group containing an acetal group, a C1-C20 alkenyl group containing a ketal group, a C1-C20 alkenyl group containing an ether group, a C6-C20 aryl group, a C6-C20 aryl group containing an acetal group, a C6-C20 aryl group containing a ketal group, a C6-C20 aryl group containing an ether group, a C1-C20 silyl group, a C1-C20 silyl group containing an acetal group, a C1-C20 silyl group containing a ketal group, and a C1-C20 silyl group containing an ether group, or $R_1$ and $R_2$ are linked to each other to form a ring, or $R_2$ and $R_3$ are linked to each other to form a ring, or $R_4$ and $R_5$ are linked to each other to form a ring;

E is O, S or N—R; said R is a methyl group, a benzene ring, or a substituted benzene ring;

$X_1$ and $X_2$ are each independently selected from one of a C1-C20 silyl group, an allyl group, and an allyl derivative; said substituted phenyl group is a phenyl group substituted by one or more of a C1-C20 aliphatic group, a C1-C20 alicyclic group, and an aromatic group;

L is a neutral Lewis base, and w is an integer of 0-3.

Here, said Ln, $R_1$, $R_2$, $R_3$, $R_4$, $R_5$, E, $X_1$, $X_2$, and L are all as described above, and verbose words are omitted hereby.

The sources of all raw materials in this invention are not particularly limited, and those commercially available may be used. Said cyclopentadienyl ligand represented by formula (II) may be commercially available or may also be prepared according to the reported methods, and is not particularly limited.

When the cyclopentadienyl ligand represented by formula (II) is a thiophene-fused cyclopentadienyl ligand, it may be prepared according to the following scheme:

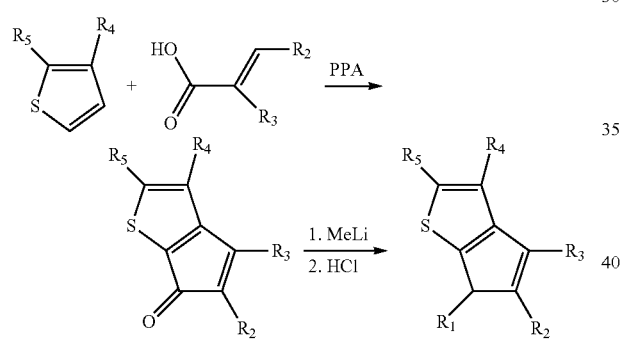

or may also be prepared according to the following scheme:

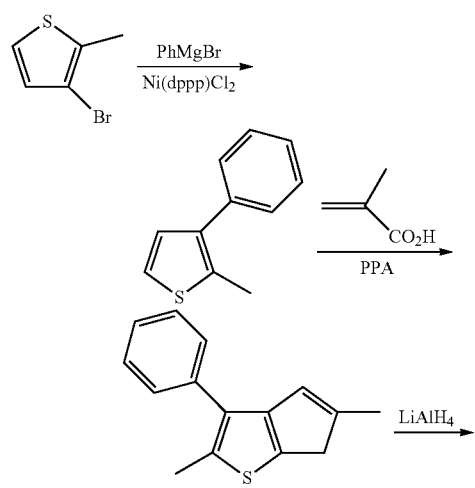

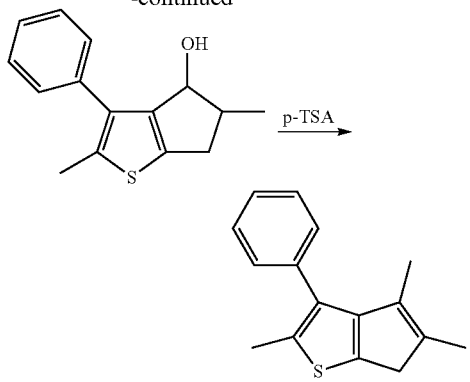

When the cyclopentadienyl ligand represented by formula (II) is a pyrrole-fused cyclopentadienyl ligand, it is preferably prepared according to the following scheme:

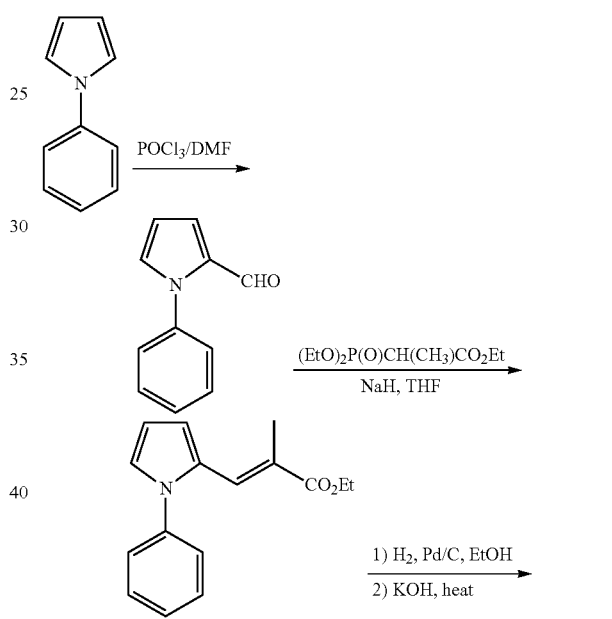

Here, said inert gas is not particularly limited, as long as it is an inert gas well known by the person skilled in the art, and it is preferably nitrogen gas or argon gas in this invention. A reaction of a cyclopentadienyl ligand represented by formula (II) and a rare earth compound is performed in a first organic solvent under the protective condition of an inert gas, wherein said first organic solvent is not particularly limited, as long as it is an organic solvent well known by the person skilled in the art, and it is preferably n-hexane in this invention; the molar ratio of the cyclopentadienyl ligand represented by formula (II) to the rare earth compound is preferably 1:(1-1.2), more preferably 1:1; and the reaction time of the cyclopentadienyl ligand represented by formula (II) and the rare earth compound performed in the first organic solvent is preferably 6-15 h, more preferably 6-14 h, still more preferably 6-12 h.

After completion of the reaction, the reaction liquid is preferably concentrated, and the metallocene complex represented by formula (I) is obtained after recrystallization.

When $X_1$ and $X_2$ in the metallocene complex represented by formula (I) are each independently an allyl group or an allyl derivative, the metallocene complex represented by formula (I) is prepared according to the following step of: performing a first reaction of a cyclopentadienyl ligand represented by formula (II) and an alkyl lithium in a second organic solvent under the protective condition of an inert gas, then performing a second reaction by adding a rare earth halide, and performing a third reaction by further adding an allyl Grignard reagent and/or an allyl derivative Grignard reagent to obtain a metallocene complex represented by formula (I) wherein $X_1$ and $X_2$ are each independently an allyl group or an allyl derivative.

Here, said inert gas is an inert gas well known by the person skilled in the art, and it is preferably nitrogen gas. A first reaction of a cyclopentadienyl ligand represented by formula (II) and an alkyl lithium is performed in a second organic solvent under the protective condition of an inert gas, wherein the molar ratio thereof is preferably 1:(1-1.2), more preferably 1:1; said alkyl lithium is not particularly limited, as long as it is an alkyl lithium well known by the person skilled in the art, and it is preferably n-butyl lithium in this invention; said second organic solvent is not particularly limited, as long as it is an organic solvent well known by the person skilled in the art, and it is preferably tetrahydrofuran in this invention; and according to this invention, the cyclopentadienyl ligand represented by formula (II) is preferably first dissolved in a second organic solvent and is placed in an environment at −78° C.-0° C., and an alkyl lithium is then added to perform a first reaction. In order to stabilize the reaction temperature, the alkyl lithium is preferably dissolved in an organic solvent and is then added to the reaction system. The organic solvent for dissolving the alkyl lithium may be the same as the second organic solvent or may also be different therefrom, and it is not particularly limited, preferably n-hexane in this invention; The alkyl lithium is dissolved in an organic solvent, and the amount of the organic solvent is preferably such that the concentration of the alkyl lithium is 1.0-2.0 mol/L. A first reaction is performed after the alkyl lithium is added, and the temperature of said first reaction is preferably −78° C.~0° C., more preferably −50° C.~0° C., still more preferably −10° C.~0° C.; and the time of said first reaction is preferably 0.8~1.5 h, more preferably 0.8~1.2 h, still more preferably 1 h.

After the first reaction, a rare earth halide is added to perform a second reaction. Here, said rare earth halide is not particularly limited, as long as it is a rare earth halide well known by the person skilled in the art, and it is preferably a rare earth trichloride in this invention; the molar ratio of the rare earth halide to the cyclopentadienyl ligand represented by formula (II) is preferably (1-1.2):1, more preferably 1:1; and the time of the second reaction performed after the rare earth halide is added is preferably 3-5 h, more is preferably a 3.5-4.5 h, still more preferably 4 h.

After the second reaction, an allyl Grignard reagent and/or an allyl derivative Grignard reagent is added, wherein said allyl Grignard reagent is preferably $C_3H_5MgCl$; said allyl derivative Grignard reagent is preferably $C_3H_nR_6MgCl$, and said n is 3 or 4; said $R_6$ is as described above, and verbose words are omitted hereby; and the molar ratio of the allyl Grignard reagent and/or allyl derivative Grignard reagent to the cyclopentadienyl ligand represented by formula (II) is preferably (2-2.4):1, more preferably 2:1.

A third reaction is performed after the allyl Grignard reagent and/or allyl derivative Grignard reagent is added. Said third reaction is preferably performed at room temperature, and the reaction time thereof is preferably 10-14 h, more preferably 11-13 h, still more preferably 12 h.

After the third reaction, the solvent is preferably removed, and by extraction with toluene and concentration, the metallocene complex represented by formula (I) wherein $X_1$ and $X_2$ are each independently an allyl group or an allyl derivative is obtained.

This invention further provides a catalyst composition, comprising a metallocene complex represented by formula (I) and an organic boron salt.

According to this invention, said organic boron salt is an activating agent, which is an ionic compound.

The cationic portion of this ionic compound is preferably one or more of a carbonium cation, an oxonium ion, an ammonium cation, a phosphonium cation. Here, said carbonium cation is preferably a (triphenyl)carbonium cation and/or a tris(substituted phenyl)carbonium cation; said tris(substituted phenyl)carbonium cation is preferably one or more of tris(methylphenyl)carbonium cation, a tris(dimethylphenyl)carbonium cation, and a tris(trimethylphenyl)carbonium cation; said ammonium cation is preferably one or more of a trimethyl ammonium cation, a triethyl ammonium cation, a tripropyl ammonium cation, and a tributyl ammonium cation; and said phosphonium cation is preferably one or more of a triphenyl phosphonium cation, a trimethylphenyl phosphonium cation, and a tris(xylenyl)phosphonium cation.

The anionic portion of this ionic compound is preferably a tetravalent boron anion. Said tetravalent boron anion is not particularly limited, as long as it is a tetravalent boron anion well known by the person skilled in the art, and it is preferably one or more of a tetrakis(phenyl)boron anion, a tetrakis(monofluorophenyl)boron anion, a tetrakis(difluorophenyl)boron anion, a tetrakis(tetrafluoro-methyl-phenyl) boron anion, and a tetrakis(pentafluorophenyl)boron anion in this invention.

Said ionic compound in this invention may be a combined product of any anion and any cation described above, and it is preferably $[Ph_3C][B(C_6F_5)_4]$, $[PhMe_2NH][B(C_6F_5)_4]$, or a neutral compound containing boron $B(C_6F_5)_3$, more preferably $[Ph_3C][B(C_6F_5)_4]$.

In the catalyst composition of this invention, the molar ratio of the organic boron salt to the metallocene complex represented by formula (I) is preferably (0.5-10):1, more preferably (1-5): 1, still more preferably (1-3): 1.

According to this invention, this catalyst composition preferably further comprises an alkyl aluminum. Said alkyl aluminum is preferably one or more of trimethyl aluminum, triethyl aluminum, tri-n-propyl aluminum, tri-n-butyl aluminum, triisopropyl aluminum, triisobutyl aluminum, tripentyl aluminum, trihexyl aluminum, tricyclohexyl aluminum, trioctyl aluminum, triphenyl aluminum, tri-p-tolyl aluminum, tribenzyl aluminum, ethyldibenzyl aluminum, ethyl-di-p-tolyl aluminum, and diethylbenzyl aluminum. In the catalyst composition, the molar ratio of the alkyl aluminum to the metallocene complex represented by formula (I) is preferably (2-200):1, more preferably (2-100):1, still more preferably (5-50):1.

The catalyst composition of this invention may be used for catalyzing the polymerization reaction of one or more of styrene, substituted styrene, ethylene, α-olefins, cyclic olefins, and non-conjugated dienes. Said α-olefin monomer is preferably a C2-C20 α-olefin, more preferably 1-hexene or 1-octene; said cyclic olefin is preferably a C5-C20 cyclic olefin, more preferably a C5-C12 cyclic olefin, still more preferably a norbornene (NB) type cyclic olefin, dicyclopentadiene (DCPD), or cyclohexadiene; and said non-conjugated dialkene is preferably a C4-C20 diene or a substituted diene, more preferably a C4-C10 diene or a substituted diene, still more preferably 1,3-hexadiene, 1,4-hexadiene, 1,5-hexadiene, 2,4-dimethyl-1,3-pentadiene, 2-methyl-1,3-hexadiene, or 2,4-hexadiene.

The catalyst, which is the metallocene complex represented by formula (I), used in the catalyst composition, does not contain any side chain, and the coordination space of the central metal has a large opening degree. Therefore, the catalytic activity for more sterically hindered monomers is higher, and the comonomer incorporation is also higher. Furthermore, the metallocene complex represented by formula (I) used in this invention is a heterocyclic ring fused cyclopentadienyl ligand. Heterocyclic rings have relatively strong electron-donating capacity. By fusing a cyclopentadienyl group using heterocyclic rings, it is possible to change the electronic effect of the metal center and in turn increase the activity of catalyst. Therefore, by using the metallocene complex represented by formula (I), it is possible to prepare copolymers of ethylene with other alkenes at high activity and high comonomer incorporation, and it is also possible to prepare styrene and substituted styrene at high syndiotacticity and high activity.

This invention further provides a preparation method of a polymer, which comprises mixing the catalyst composition described above with an alkene monomer and performing a polymerization reaction to obtain the polymer.

Here, said alkene monomer is selected from one or more of styrene, substituted styrene, ethylene, α-olefins, cyclic olefins, and non-conjugated dienes. Said substituted styrene, α-olefins, cyclic olefins, and non-conjugated dienes are all as described above, and verbose words are omitted hereby.

For mixing the catalyst composition with an alkene monomer, it is preferable that after the catalyst composition is mixed, a reaction is activated for 0.5-10 min, more preferably 1-5 min, still more preferably 1 min, and then the alkene monomer is mixed to perform a polymerization reaction. The conditions of the polymerization reaction are not particularly limited, as long as they are conditions well known by the person skilled in the art, and in this invention, the temperature of the polymerization reaction is preferably 20° C.-60° C., more preferably 25° C.-40° C.; the time of the polymerization reaction is preferably 5-100 min, more preferably 5-60 min.

After the polymerization reaction, a hydrochloric acid-ethanol solution is preferably used to terminate the reaction. In said hydrochloric acid-ethanol solution, the volume ratio of hydrochloric acid to ethanol is preferably a 1:(5~15), more preferably 1:(8~12), still more preferably 1:10.

After the reaction is terminated, the reaction solution is preferably poured into ethanol for settling, and a polymer is obtained by filtration.

It is experimentally demonstrated that the catalyst composition of this invention exhibits features such as high activity, high comonomer incorporation of copolymerization monomers, etc., in catalysis of copolymerization reactions of ethylene with styrene, α-olefins, cyclic olefins, and non-conjugated dienes.

In order to further illustrate this invention, the detailed description will be made in conjunction with the Examples below, with respect to the metallocene complex and the preparation method thereof and the catalyst composition provided by this invention.

All reagents used in the Examples below are commercially available.

Example 1

Under the protective condition of nitrogen gas, 0.3 g (1.56 mmol) of a thiophene-fused cyclopentadienyl ligand 1 was dissolved in 8 ml of n-hexane and was dropped to a n-hexane solution containing 0.7 g (1.56 mmol) of $Sc(CH_2SiMe_3)_3$ $(thf)_2$, a reaction was performed for 12 h, the reaction solution was concentrated, and recrystallization was performed to obtain 0.57 g of a light yellow thiophene-fused metallocene type scandium alkyl complex (I-1) with a molecular formula of $C_{22}H_{41}OSScSi_2$, wherein the yield was 75% and the reaction formula was as follows:

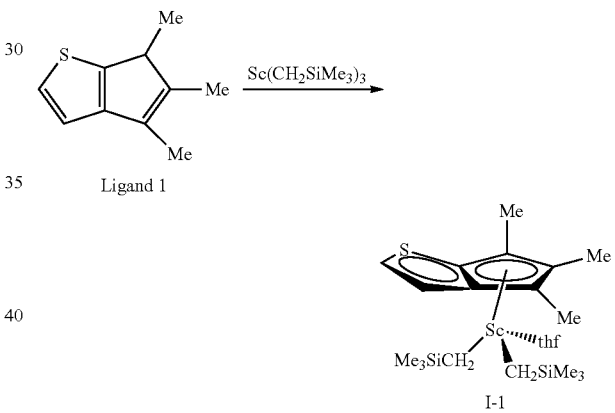

The metallocene type scandium alkyl complex (I-1) obtained in Example 1 was analyzed using elemental analysis to obtain a result of elemental analysis (%): C, 58.52; H, 8.85.

Example 2

The steps were the same as those in Example 1 except that ligand 1 in Example 1 was replaced by ligand 2 such that a thiophene-fused metallocene type scandium alkyl complex (I-2) with a molecular formula of $C_{24}H_{45}OSScSi_2$ was obtained, and the reaction formula was as follows:

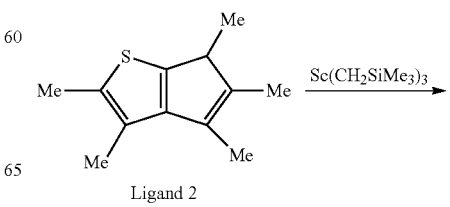

-continued

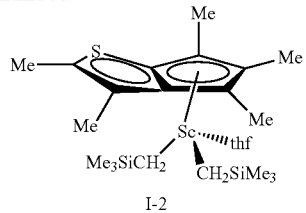
I-2

The metallocene type scandium alkyl complex (I-2) obtained in Example 2 was analyzed using nuclear magnetic resonance to obtain a hydrogen nuclear magnetic resonance spectrogram thereof as shown in FIG. 1. The result of nuclear magnetic resonance is:

$^1$H NMR(C$_6$D$_6$, 25° C.): δ 3.59 (br s, 2H, THF), 3.50 (br s, 2H, THF), 2.41 (s, 3H), 2.19 (s, 3H), 2.15 (s, 6H), 2.09 (s, 1H), 1.19 (br s, 4H), 0.30 (s, 18H, CH$_2$SiMe$_3$), −0.23 (br s, 2H, CH$_2$SiMe$_3$), −0.28 (d, J=0.08 Hz, 1H, CH$_2$SiMe$_3$), −0.37 (d, J=0.08 Hz, 1H, CH$_2$SiMe$_3$) ppm.

$^{13}$CNMR(C$_6$D$_6$, 25° C.): δ 133.31, 130.43, 126.24, 124.77, 121.80, 110.18, 109.12, 71.54, 24.96, 24.77, 13.87, 13.30, 13.03, 12.68, 12.64, 12.28, 4.34 ppm.

The metallocene type scandium alkyl complex (1-2) obtained in Example 2 was analyzed using elemental analysis to obtain a result of elemental analysis (%): C, 59.96; H, 9.68.

Example 3

The steps were the same as those in Example 1 except that ligand 1 in Example 1 was replaced by ligand 3 such that a thiophene-fused metallocene type scandium alkyl complex (I-3) with a molecular formula of C$_{23}$H$_{43}$OSScSi$_2$ was obtained, and the reaction formula was as follows:

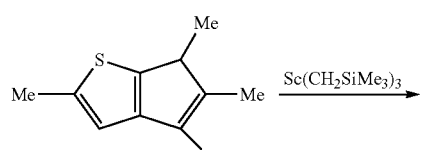

Figure 2:
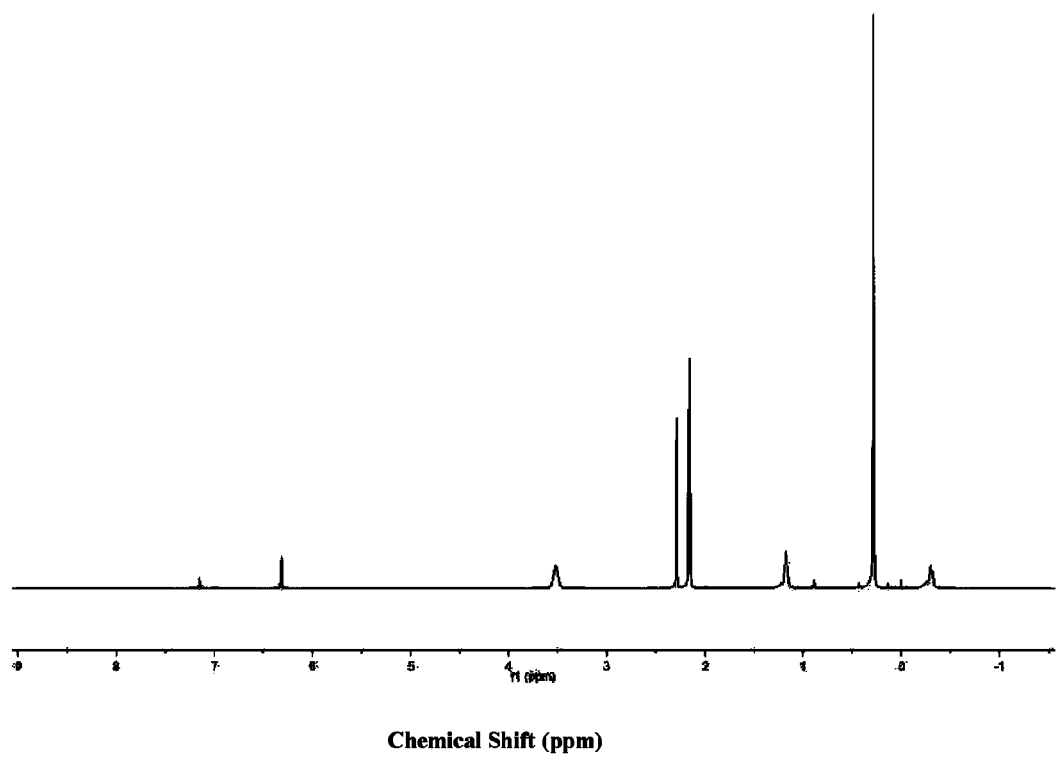
FIG. 2 is a hydrogen nuclear magnetic resonance spectrogram of a metallocene type scandium alkyl complex (I-3) obtained in Example 3 of this invention.

The metallocene type scandium alkyl complex (I-3) obtained in Example 3 was analyzed using nuclear magnetic resonance to obtain a hydrogen nuclear magnetic resonance spectrogram thereof as shown in FIG. 2. The result of nuclear magnetic resonance is:

$^1$H NMR(C$_6$D$_6$, 25° C.): δ 6.32 (s, 1H), 3.59 (br s, 4H), 2.29 (s, 3H), 2.17 (s, 3H), 2.16 (s, 6H), 1.18 (br s, 4H), 0.29 (s, 18H), −0.20 (s, 4H) ppm.

$^{13}$CNMR(C$_6$D$_6$, 25° C.): δ 138.15, 132.56, 125.94, 123.86, 116.28, 109.77, 109.18, 71.46, 25.34, 24.94, 16.54, 16.20, 13.39, 13.12, 12.51, 4.41 ppm.

The metallocene type scandium alkyl complex (I-3) obtained in Example 3 was analyzed using elemental analysis to obtain a result of elemental analysis (%): C, 59.32; H, 9.64.

Example 4

The conditions and steps were the same as those in Example 1 except that the ligands and the rare earth compounds were correspondingly replaced such that metallocene complexes I-4~I-9 were prepared. Raw materials for preparing metallocene complexes I-4~I-9 and results thereof can be seen in Table 1.

TABLE 1

| Raw materials for preparing metallocene complexes I-4~I-9 and results | | | | | |
|---|---|---|---|---|---|
| Metallocene complex | Ligand | Rare earth compound | Molecular formula of target compounds | Elemental analysis (%) | Yield (%) |
| I-4 | Ligand 1 | Y(CH$_2$SiMe$_3$)$_3$ | C$_{22}$H$_{41}$OSYSi$_2$ | C 52.56, H 8.52 | 58 |
| I-5 | Ligand 2 | Y(CH$_2$SiMe$_3$)$_3$ | C$_{24}$H$_{45}$OSYSi$_2$ | C 54.32, H 8.96 | 65 |
| I-6 | Ligand 3 | Y(CH$_2$SiMe$_3$)$_3$ | C$_{23}$H$_{43}$OSYSi$_2$ | C 53.79, H 8.83 | 62 |
| I-7 | Ligand 1 | Er(CH$_2$SiMe$_3$)$_3$ | C$_{22}$H$_{41}$OSErSi$_2$ | C 45.98, H 7.42 | 75 |
| I-8 | Ligand 2 | Er(CH$_2$SiMe$_3$)$_3$ | C$_{24}$H$_{45}$OSErSi$_2$ | C 47.36, H 7.87 | 69 |
| I-9 | Ligand 3 | Er(CH$_2$SiMe$_3$)$_3$ | C$_{23}$H$_{43}$OSErSi$_2$ | C 46.99, H 6.95 | 64 |

Example 5

Under the protective condition of nitrogen gas, 0.23 g (1.00 mmol) of a thiophene-fused cyclopentadienyl ligand 4 was dissolved in 5 ml of n-hexane and was dropped to a n-hexane solution containing 0.45 g (1.00 mmol) of Sc(CH$_2$SiMe$_3$)$_3$(thf)$_2$, a reaction was performed for 12 h, the reaction solution was concentrated, and recrystallization was performed to obtain 0.37 g of a light yellow thiophene-fused metallocene type scandium alkyl complex (I-10) with a molecular formula of C$_{27}$H$_{43}$OSScSi$_2$, wherein the yield was 72% and the reaction formula was as follows:

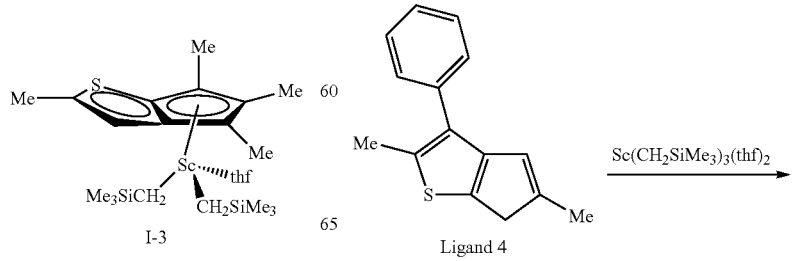

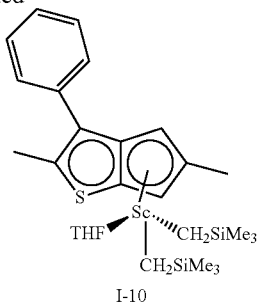

I-10

The metallocene type scandium alkyl complex (I-10) obtained in Example 5 was analyzed using elemental analysis to obtain a result of elemental analysis (%): C, 62.95; H, 8.45.

Example 6

By using the synthetic scheme of Example 5, a thiophene-fused cyclopentadienyl ligand 4 (0.23 g, 1.00 mmol) was reacted with a trialkyl yttrium complex $Y(CH_2SiMe_3)_3(thf)_2$ and a trialkyl dysprosium complex $Dy(CH_2SiMe_3)_3(thf)_2$ respectively to obtain metallocene complexes I-11 and I-12. The molecular formula of the metallocene complex I-11 was $C_{27}H_{43}OSYSi_2$ and the yield thereof was 69%; and the molecular formula of the metallocene complex I-12 was $C_{27}H_{43}OSDy Si_2$ and the yield thereof was 72%.

The metallocene complex I-11 obtained in Example 6 was analyzed using elemental analysis to obtain a result of elemental analysis (%): C, 57.49; H, 8.09.

The metallocene complex I-12 obtained in Example 6 was analyzed using elemental analysis to obtain a result of elemental analysis (%): C, 51.36; H, 7.14.

Example 7

Under the protective condition of nitrogen gas, 0.3 g (2.04 mmol) of a pyrrole-fused cyclopentadienyl ligand 5 was dissolved in 5 ml of n-hexane and was dropped to a n-hexane solution containing 0.92 g (2.04 mmol) of $Sc(CH_2SiMe_3)_3$ $(thf)_2$, a reaction was performed for 6 h, the reaction solution was concentrated, and recrystallization was performed to obtain 0.56 g of a light yellow pyrrole-fused metallocene type scandium alkyl complex (I-13) with a molecular formula of $C_{22}H_{42}NOScSi_2$, wherein the yield was 63% and the reaction formula was as follows:

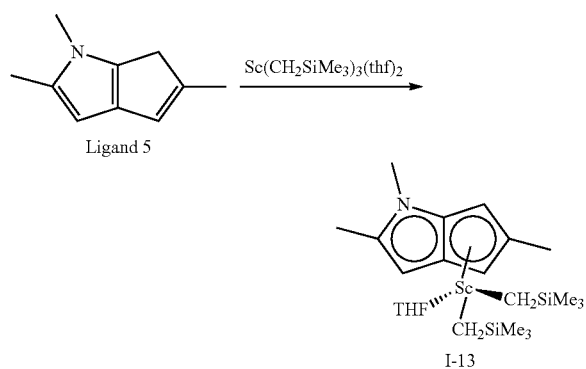

The metallocene type scandium alkyl complex (I-13) obtained in Example 7 was analyzed using elemental analysis to obtain a result of elemental analysis (%): C, 60.68; H, 9.44; N 3.45.

Example 8

By using the synthetic scheme of Example 7, a pyrrole-fused cyclopentadienyl ligand 5 (0.30 g, 2.04 mmol) was reacted with a trialkyl yttrium complex $Y(CH_2SiMe_3)_3(thf)_2$ and a trialkyl gadolinium complex $Gd(CH_2SiMe_3)_3(thf)_2$ respectively to obtain metallocene complexes I-14 and I-15. The molecular formula of the metallocene complex I-14 was $C_{22}H_{42}NOYSi_2$ and the yield thereof was 64%; and the molecular formula of the metallocene complex I-15 was $C_{22}H_{42}NOGdSi_2$ and the yield thereof was 62%.

The metallocene complex I-14 obtained in Example 8 was analyzed using elemental analysis to obtain a result of elemental analysis (%): C, 54.78; H, 8.43; N 2.68.

The metallocene complex I-15 obtained in Example 8 was analyzed using elemental analysis to obtain a result of elemental analysis (%): C, 48.36; H, 7.43; N 2.69.

Example 9

Under the protective condition of nitrogen gas, 0.3 g (1.43 mmol) of a pyrrole-fused cyclopentadienyl ligand 6 was dissolved in 5 ml of n-hexane and was dropped to a n-hexane solution containing 0.65 g (1.43 mmol) of $Sc(CH_2SiMe_3)_3$ $(thf)_2$, a reaction was performed for 8 h, the reaction solution was concentrated, and recrystallization was performed to obtain 0.38 g of a light yellow pyrrole-fused metallocene type scandium alkyl complex (I-16) with a molecular formula of $C_{27}H_{44}NOScSi_2$, wherein the yield thereof was 53% and the reaction formula was as follows:

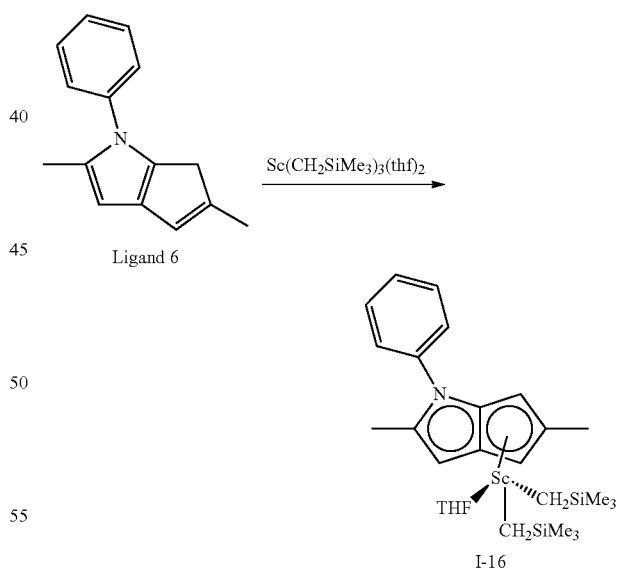

The metallocene type scandium alkyl complex (I-16) obtained in Example 9 was analyzed using elemental analysis to obtain a result of elemental analysis (%): C, 64.68; H, 8.75; N 3.12.

Example 10

By using the synthetic scheme of Example 9, a pyrrole-fused cyclopentadienyl ligand 6 (0.30 g, 1.43 mmol) was reacted with a trialkyl yttrium complex Y(CH$_2$SiMe$_3$)$_3$(thf)$_2$ and a trialkyl lutetium complex Lu(CH$_2$SiMe$_3$)$_3$(thf)$_2$ respectively to obtain a metallocene complex I-17 and a metallocene complex I-18. The molecular formula of the metallocene complex I-17 was C$_{27}$H$_{44}$NOYSi$_2$ and the yield thereof was 66%; and the molecular formula of the metallocene complex I-18 was C$_{27}$H$_{44}$NOLuSi$_2$ and the yield thereof was 62%.

The metallocene complex I-17 obtained in Example 10 was analyzed using elemental analysis to obtain a result of elemental analysis (%): C, 59.78; H, 8.43; N 2.68.

The metallocene complex I-18 obtained in Example 8 was analyzed using elemental analysis to obtain a result of elemental analysis (%): C, 51.69; H, 7.43; N 2.59.

Example 11

Under the protective condition of nitrogen gas, 0.23 g (1.2 mmol) of a thiophene-fused cyclopentadienyl ligand 2 was dissolved in tetrahydrofuran and was placed at −78° C.-0° C., 1.2 mmol of a n-hexane solution of n-butyl lithium (the concentration was 1.0-2.0 mol/L) was then added, 1.2 mmol of scandium trichloride ScCl$_3$ was added after reacting for 1 h, 2.4 mmol of C$_3$H$_5$MgCl was added after reacting for 4 h. The solvent was removed after reacting at room temperature for 12 h, extraction was performed with toluene, and a toluene solution was concentrated to obtain 0.25 g of a thiophene-fused metallocene complex I-19 with a molecular formula of C$_{18}$H$_{25}$SSc, wherein the yield thereof was 64% and the reaction formula was as follows:

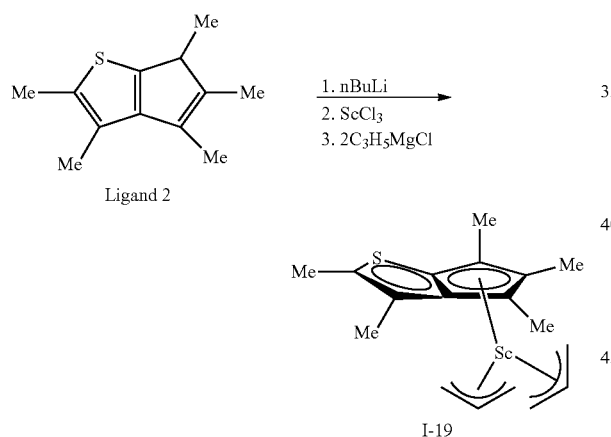

The metallocene complex I-19 obtained in Example 11 was analyzed using elemental analysis to obtain a result of elemental analysis (%): C, 68.22; H, 7.66.

Example 12

By using the synthetic scheme of Example 11, a thiophene-fused cyclopentadienyl ligand 2 (0.23 g, 1.2 mmol) was reacted with yttrium trichloride YCl$_3$ and gadolinium trichloride GdCl$_3$ respectively to obtain a metallocene complex I-20 and a metallocene complex I-21. The molecular formula of the metallocene complex I-20 was C$_{18}$H$_{25}$SY and the yield thereof was 65%; and the molecular formula of the metallocene complex I-21 was C$_{18}$H$_{25}$SGd and the yield thereof was 68%.

The metallocene complex I-20 obtained in Example 12 was analyzed using elemental analysis to obtain a result of elemental analysis (%): C, 59.78; H, 6.61.

The metallocene complex I-21 obtained in Example 12 was analyzed using elemental analysis to obtain a result of elemental analysis (%): C, 49.83; H, 6.04.

Example 13

Under the protective condition of nitrogen gas, 0.30 g (1.43 mmol) of a pyrrole-fused cyclopentadienyl ligand 6 was dissolved in tetrahydrofuran and was placed at −78° C.-0° C., 1.43 mmol of a n-hexane solution of n-butyl lithium (concentration was 1.0-2.0 mol/L) was then added, 1.43 mmol of scandium trichloride ScCl$_3$ was added after reacting for 1 h, 2.86 mmol of C$_3$H$_5$MgCl was added after reacting for 4 h. The solvent was removed after reacting at room temperature for 12 h, extraction was performed with toluene, and a toluene solution was concentrated to obtain 0.27 g of a pyrrole-fused metallocene complex I-22 with a molecular formula of C$_{21}$H$_{24}$NSc, wherein the yield thereof was 63% and the reaction formula was as follows:

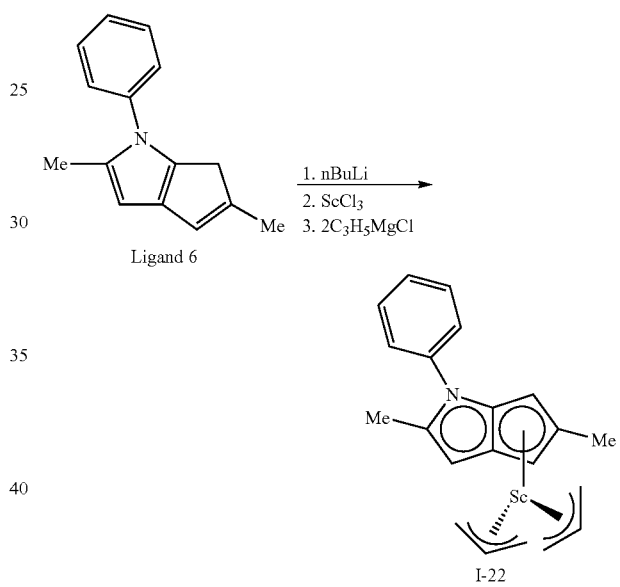

The metallocene complex I-22 obtained in Example 13 was analyzed using elemental analysis to obtain a result of elemental analysis (%): C, 75.44; H, 7.54; N 3.79.

Example 14

By using the synthetic scheme of Example 13, a pyrrole-fused cyclopentadienyl ligand 6 (0.30 g, 1.43 mmol) was reacted with yttrium trichloride YCl$_3$ and lutetium trichloride LuCl$_3$ respectively to obtain a metallocene complex 23 and a metallocene complex 24. The molecular formula of the metallocene complex 23 was C$_{21}$H$_{24}$NY and the yield thereof was 68%; and the molecular formula of the metallocene complex 24 was C$_{21}$H$_{24}$NLu and the yield thereof was 72%.

The metallocene complex I-23 obtained in Example 14 was analyzed using elemental analysis to obtain a result of elemental analysis (%): C, 66.26; H, 6.64; N 4.02.

The metallocene complex I-24 obtained in Example 14 was analyzed using elemental analysis to obtain a result of elemental analysis (%): C, 43.86; H, 5.57; N 3.37.

Example 15

In 20 ml of a polymerization flask which was treated without water and oxygen, 10 μmol of the metallocene complex I-1 obtained in Example 1. 3 ml of a toluene solution containing 10 μmol of $[Ph_3C][B(C_6F_5)_4]$ were added, 0.2 ml of $Al(^iBu)_3$ (0.5 mol/L) was dropped, 10 mmol of a styrene monomer (the molar ratio of the monomer to the metallocene complex I-1 was 1000:1) was added in this catalyst system after reacting for 1 min, and the polymerization flask was set in the thermo stated water bath (25° C.). A reaction was performed for 5 min with stirring, and 2 ml of a hydrochloric acid-ethanol solution (v/v, 1:10) was further added to terminate the polymerization reaction. The reaction solution was poured into 100 ml of ethanol for settling to obtain polystyrene, which was a white solid. The white solid polystyrene was filtered and washed with ethanol, and then dried under vacuum at 40° C. for 48 h to obtain a dry white solid powder of polystyrene with a net weight of 1.04 g, and the conversion was 100%.

Polystyrene obtained in Example 15 was analyzed with a high-temperature GPC to determine that it had a number average molecular weight ($M_n$) of 127,000 and a molecular weight distribution ($M_w/M_n$) of 1.42.

Polystyrene obtained in Example 15 was analyzed with nuclear magnetic resonance to determine that this polystyrene had a syndiotacticity (rrrr) of 99%.

Polystyrene obtained in Example 15 was analyzed with a differential scanning calorimetry (DSC) to determine that it has two melting points $T_m$, 262° C. and 271° C.

Example 16

Polystyrene was prepared according to the method of Example 15, except that the input amount of styrene was changed to 5 mmol.

Example 17

Polystyrene was prepared according to the method of Example 15, except that the input amount of styrene was changed to 15 mmol.

Example 18

Polystyrene was prepared according to the method of Example 15, except that the input amount of styrene was changed to 20 mmol.

Example 19

Polystyrene was prepared according to the method of Example 15, except that the metallocene complex I-1 obtained in Example 1 was replaced by the metallocene complex I-2 obtained in Example 2.

Example 20

Polystyrene was prepared according to the method of Example 15, except that the metallocene complex I-1 obtained in Example 1 was replaced by the metallocene complex I-3 obtained in Example 3.

Example 21

Polystyrene was prepared according to the method of Example 15, except that the metallocene complex I-1 obtained in Example 1 was replaced by the metallocene complex I-4 obtained in Example 4 while the time of the polymerization reaction was changed to 30 min.

Example 22

Polystyrene was prepared according to the method of Example 15, except that the metallocene complex I-1 obtained in Example 1 was replaced by the metallocene complex I-5 obtained in Example 4 while the time of the polymerization reaction was changed into 30 min.

Example 23

Polystyrene was prepared according to the method of Example 15, except that the metallocene complex I-1 obtained in Example 1 was replaced by the metallocene complex I-6 obtained in Example 4 while the time of the polymerization reaction was changed into 30 min.

Example 24

Polystyrene was prepared according to the method of Example 15, except that the metallocene complex I-1 obtained in Example 1 was replaced by the metallocene complex I-8 obtained in Example 4 while the time of the polymerization reaction was changed into 60 min.

Example 25

In 20 ml of a polymerization flask which was treated without water and oxygen, 10 μmol of the metallocene complex I-10 obtained in Example 5 was added, 10 μmol of $[Ph_3C][B(C_6F_5)_4]$ and 3 ml of toluene were mixed, 0.2 ml of $Al(^iBu)_3$ (0.5 mol/L) was dropped, 10 mmol of a styrene monomer (the molar ratio of the monomer to the metallocene complex I-10 was 1000:1) was added in this catalyst system after reacting for 1 min. The polymerization flask was set in the thermo stated water bath (25° C.), a reaction was performed for 10 min with stirring, and 2 ml of a hydrochloric acid-ethanol solution (v/v, 1:10) was further added to terminate the polymerization reaction. The reaction solution was poured into 100 ml of ethanol for settling to obtain a white solid, polystyrene, which was filtered and washed with ethanol, and then dried under vacuum at 40° C. for 48 h to obtain a dry white solid powder of polystyrene with a net weight of 1.04 g, and the conversion was 100%.

Polystyrene obtained in Example 25 was analyzed with a high-temperature GPC to determine that it had a number average molecular weight ($M_n$) of 116,000 and a molecular weight distribution ($M_w/M_n$) of 1.46.

Polystyrene obtained in Example 25 was analyzed with nuclear magnetic resonance to determine that this polystyrene had a syndiotacticity (rrrr) of 99%.

Polystyrene obtained in Example 25 was analyzed with a differential scanning calorimetry (DSC) to determine that it has a melting point $T_m$ of 271° C.

Example 26

Polystyrene was prepared according to the method of Example 25, except that the metallocene complex I-10 obtained in Example 25 was replaced by the metallocene complex I-20 obtained in Example 12 while the time of the polymerization reaction was changed into 60 min.

Example 27

Polystyrene was prepared according to the method of Example 25, except that the metallocene complex I-10 obtained in Example 25 was replaced by the metallocene complex I-24 obtained in Example 14 while the time of the polymerization reaction was changed into 60 min.

Polystyrenes obtained in Examples 15-27 were analyzed with high-temperature GPC, nuclear magnetic resonance, and differential scanning calorimetry (DSC) to obtain the results shown in Table 2. The dry polymer was determined for the tacticity of styrene using a carbon nuclear magnetic resonance spectrogram.

Example 29

A styrene-ethylene polymer was prepared according to the method of Example 28, except that the input amount of styrene was changed to 20 mmol.

Example 30

A styrene-ethylene polymer was prepared according to the method of Example 28, except that the input amount of styrene was changed to 30 mmol.

Example 31

A styrene-ethylene polymer was prepared according to the method of Example 28, except that the metallocene complex I-2 was replaced by the metallocene complex I-10 obtained in Example 5.

TABLE 2

Result of homopolymerization of styrene

| | Metallocene complex | Styrene/complex (molar ratio) | Reaction time (min) | Conversion (%) | Polystyrene syndiotacticity (rrrr) (%) | $M_n$ ($\times 10^4$) | $M_w/M_n$ | $T_m$ (° C.) |
|---|---|---|---|---|---|---|---|---|
| Example 15 | I-1 | 1000 | 5 | 100 | 99 | 12.7 | 1.42 | 262/271 |
| Example 16 | I-1 | 500 | 5 | 100 | 99 | 6.5 | 1.68 | 271 |
| Example 17 | I-1 | 1500 | 5 | 100 | 99 | 16.8 | 1.55 | 271 |
| Example 18 | I-1 | 2000 | 5 | 100 | 99 | 26.9 | 1.32 | 271 |
| Example 19 | I-2 | 1000 | 5 | 100 | 99 | 10.8 | 1.64 | 265/272 |
| Example 20 | I-3 | 1000 | 5 | 100 | 99 | 9.7 | 1.72 | 272 |
| Example 21 | I-4 | 1000 | 30 | 91 | 99 | 9.6 | 1.53 | 270 |
| Example 22 | I-5 | 1000 | 30 | 93 | 99 | 10.4 | 1.62 | 269 |
| Example 23 | I-6 | 1000 | 30 | 89 | 98 | 9.9 | 1.45 | 267 |
| Example 24 | I-8 | 1000 | 60 | 62 | 98 | 12.3 | 1.51 | 269 |
| Example 25 | I-10 | 1000 | 10 | 100 | 98 | 11.6 | 1.46 | 271 |
| Example 26 | I-20 | 1000 | 60 | 87 | 98 | 10.4 | 1.61 | 268 |
| Example 27 | I-24 | 1000 | 60 | 42 | 98 | 13.8 | 1.75 | 270 |

Example 28

In a glove box, 30 ml of toluene and 1.04 g (10 mmol) of styrene were added to a 100 ml two-necked flask and were mixed with stirring. This flask was taken out of the glove box and was connected to a Schlenk line. The temperature of the flask was maintained at 40° C. by an oil bath, and the solution was degassed and then saturated with ethylene (1 atm) for three times under vigorous stirring. 9.2 mg (10 μmol) of [Ph$_3$C][B(C$_6$F$_5$)$_4$], 4.8 mg (10 μmol) of the metallocene complex I-2 obtained in Example 2, 0.2 ml of Al($^i$Bu)$_3$ (0.5 mol/L), and toluene were mixed and were stirred for 1 min to prepare an activated catalyst composition. The catalyst composition was rapidly injected into the flask by a syringe to initiate polymerization. The polymerization reaction was performed for 5 min with the introduction of ethylene at 1.0 atm. 2 ml of a hydrochloric acid-ethanol solution (v/v, 1:10) was added to terminate the polymerization reaction. The polymerization reaction liquid was further poured into 300 ml of ethanol for settling, and vacuum drying was performed at 40° C. for 24 h to obtain a styrene-ethylene polymer with a net weight of 0.45 g.

Figure 3:
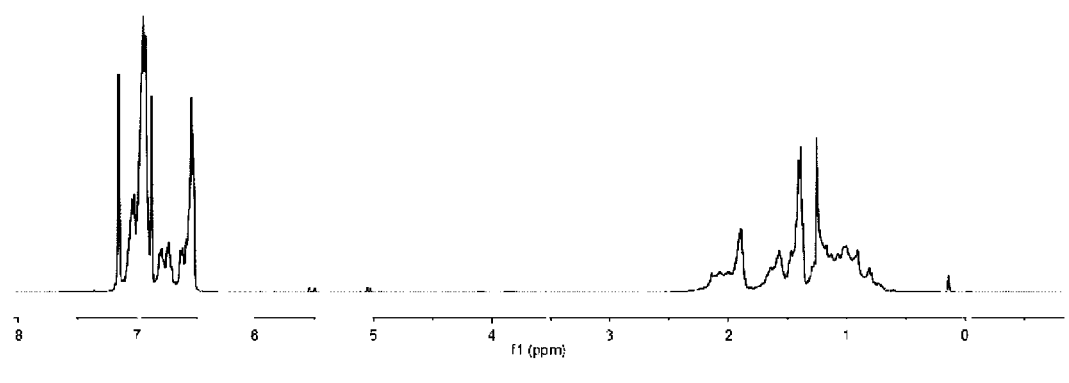
FIG. 3 is a hydrogen nuclear magnetic resonance spectrogram of a styrene-ethylene polymer obtained in Example 28 of this invention.

The styrene-ethylene polymer obtained in Example 28 was analyzed using nuclear magnetic resonance to obtain a hydrogen nuclear magnetic resonance spectrogram thereof as shown in FIG. 3.

Example 32

A styrene-ethylene polymer was prepared according to the method of Example 28, except that the metallocene complex I-2 was replaced by the metallocene complex I-13 obtained in Example 7.

Example 33

A styrene-ethylene polymer was prepared according to the method of Example 28, except that the metallocene complex I-2 was replaced by the metallocene complex I-16 obtained in Example 9.

The styrene-ethylene polymers obtained in Examples 28-33 were detected, and the number average molecular weight $M_n$ and the molecular weight distribution ($M_w/M_n$) were all determined by GPC (polystyrene was used as a reference material); the glass transition temperature and the melting point were determined by DSC method; and their performance detection results were obtained and can be seen in Table 3. The dry polymer was determined for the content of styrene using a hydrogen nuclear magnetic resonance spectrogram.

TABLE 3

Ethylene/Styrene copolymerization results

|  | Metallocene complex | Styrene (mmol) | Yield (g) | Activity ($10^6$ g/mol · $S_c$ · h) | Styrene content (mol %) | $M_n^b$ (×$10^4$) | $M_w/M_n$ | $T_m$ (° C.)$^c$ |
|---|---|---|---|---|---|---|---|---|
| Example 28 | I-2 | 10 | 0.45 | 0.54 | 61 | 8.93 | 1.35 | 213 |
| Example 29 | I-2 | 20 | 1.25 | 1.50 | 82 | 13.42 | 1.68 | 238 |
| Example 30 | I-2 | 30 | 0.63 | 0.76 | 93 | 12.87 | 1.57 | 245/265 |
| Example 31 | I-10 | 10 | 0.62 | 1.04 | 64 | 10.32 | 1.78 | 216 |
| Example 32 | I-13 | 10 | 0.54 | 0.65 | 59 | 9.12 | 1.54 | 208 |
| Example 33 | I-16 | 10 | 0.36 | 0.43 | 60 | 8.61 | 1.61 | 210 |

Example 34

In a glove box, 30 ml of toluene and 2.64 g (20 mmol) of dicyclopentadiene (DCPD) were added to a 100 ml two-necked flask and were mixed with stirring. This flask was taken out of the glove box and was connected to a Schlenk line, the temperature of the flask was maintained at 40° C. by an oil bath, and the solution was degassed and then saturated with ethylene (1 atm) for three times under vigorous stirring. 9.2 mg (10 μmol) of $[Ph_3C][B(C_6F_5)_4]$, 4.8 mg (10 μmol) of the metallocene complex I-2 obtained in Example 2, 0.1 ml of Al($^t$Bu)$_3$ (0.5 mol/L), and toluene were mixed and were stirred for 1 min to prepare an activated catalyst composition. The catalyst composition was rapidly injected into the flask by a syringe to initiate polymerization. The polymerization reaction was performed for 5 min with the introduction of ethylene at 1.0 atm, 2 ml of a hydrochloric acid-ethanol solution (v/v, 1:10) was added to terminate the polymerization reaction. The polymerization reaction liquid was further poured into 300 ml of ethanol for settling, and vacuum drying was performed at 40° C. for 24 h to obtain an ethylene-DCPD polymer with a net weight of 3.17 g.

Figure 4:
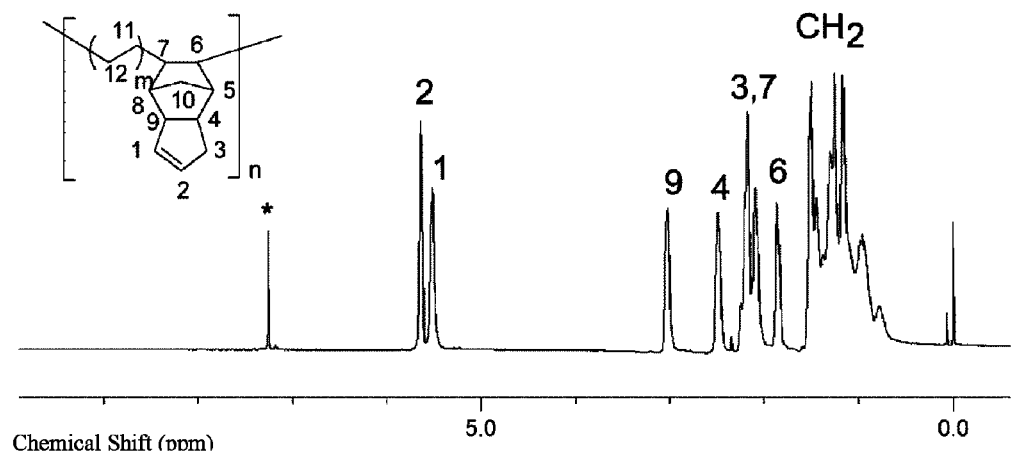
FIG. 4 is a hydrogen nuclear magnetic resonance spectrogram of an ethylene-DCPD polymer obtained in Example 34 of this invention.

The ethylene-DCPD polymer obtained in Example 34 was analyzed using nuclear magnetic resonance to obtain a hydrogen nuclear magnetic resonance spectrogram thereof as shown in FIG. 4.

Example 35

An ethylene-DCPD copolymer was prepared according to the method of Example 34, except that the input amount of DCPD was changed to 5.28 g (40 mmol) to obtain 3.01 g of a polymer.

Example 36

An ethylene-DCPD polymer was prepared according to the method of Example 35, except that the input amount of DCPD was changed to 10.56 g (80 mmol) to obtain 1.57 g of a polymer.

Example 37

An ethylene-DCPD polymer was prepared according to the method of Example 34, except that the polymerization temperature was 25° C. and 0.62 g of a polymer was obtained.

Example 38

An ethylene-DCPD polymer was prepared according to the method of Example 34, except that the polymerization temperature was 60° C. and 1.19 g of a polymer was obtained.

Example 39

An ethylene-DCPD polymer was prepared according to the method of Example 34, except that the metallocene complex I-2 was replaced by the metallocene complex I-6 obtained in Example 4 to obtain a trace amount of a flocculent polymer.

Example 40

An ethylene-DCPD polymer was prepared according to the method of Example 34, except that the metallocene complex I-2 was replaced by the metallocene complex I-10 obtained in Example 5 to obtain 2.02 g of a polymer.

Example 41

An ethylene-DCPD polymer was prepared according to the method of Example 34, except that the metallocene complex I-2 was replaced by the metallocene complex I-16 obtained in Example 9 to obtain 1.62 g of a polymer.

Example 42

An ethylene-DCPD polymer was prepared according to the method of Example 34, except that the metallocene complex I-2 was replaced by the metallocene complex I-19 obtained in Example 11 to obtain 0.89 g of a polymer.

Example 43

An ethylene-DCPD polymer was prepared according to the method of Example 34, except that the metallocene complex I-2 was replaced by the metallocene complex I-22 obtained in Example 13 to obtain 0.64 g of a polymer.

The ethylene-DCPD polymers obtained in Examples 34-43 were detected, and the number average molecular weight $M_n$ and the molecular weight distribution ($M_w/M_n$) were all determined by GPC (polystyrene was used as a reference material); the glass transition temperature and the melting point were determined by DSC method; and their performance detection results were obtained and can be seen in Table 4. The dry polymer was determined for the content of DCPD using a hydrogen nuclear magnetic resonance spectrogram (the calculation method can be seen in X. Li, Z. Hou, *Macromolecules* 2005, 38, 6767).

TABLE 4

Ethylene/DCPD copolymerization results

| | Metallocene complex | T (° C.) | DCPD (mmol) | Yield (g) | Activity (10⁶ g/mol · Ln · h) | DCPD content (mol %) | $M_n^b$ (×10⁴) | $M_w/M_n$ | $T_g$ (° C.)$^c$ |
|---|---|---|---|---|---|---|---|---|---|
| Example 34 | I-2 | 40 | 20 | 3.17 | 3.8 | 37 | 2.4 | 1.51 | 113 |
| Example 35 | I-2 | 40 | 40 | 3.01 | 3.6 | 42 | 2.1 | 1.58 | 142 |
| Example 36 | I-2 | 40 | 80 | 1.57 | 0.9 | 44 | 5.5 | 2.21 | 147 |
| Example 37 | I-2 | 25 | 20 | 0.62 | 0.5 | 20 | 1.4 | 1.46 | 126 |
| Example 38 | I-2 | 60 | 20 | 1.19 | 1.2 | 30 | 1.1 | 1.57 | 97 |
| Example 39 | I-6 | 40 | 20 | Trace | — | — | — | — | — |
| Example 40 | I-10 | 40 | 20 | 2.02 | 2.4 | 35 | 3.1 | 1.62 | 105 |
| Example 41 | I-16 | 40 | 20 | 1.62 | 1.9 | 38 | 1.8 | 1.52 | 115 |
| Example 42 | I-19 | 40 | 20 | 0.89 | 1.1 | 34 | 1.5 | 1.63 | 102 |
| Example 43 | I-22 | 40 | 20 | 0.64 | 0.8 | 34 | 1.7 | 1.51 | 99 |

Example 44

In a glove box, 30 ml of toluene and 2.24 g (20 mmol) of 1-octene were added to a 100 ml two-necked flask and were mixed with stirring. This flask was taken out of the glove box and was connected to a Schlenk line. The temperature of the flask was maintained at 40° C. by an oil bath, and then saturated with ethylene (1 atm) for three times under vigorous stirring. 9.2 mg (10 µmol) of [Ph$_3$C][B(C$_6$F$_5$)$_4$], 4.8 mg (10 µmol) of the metallocene complex I-2 obtained in Example 2, 0.1 ml of Al($^i$Bu)$_3$ (0.5 mol/L), and toluene were mixed and were stirred for 1 min to prepare an activated catalyst composition. The catalyst composition was rapidly injected into the flask by a syringe to initiate polymerization, the polymerization reaction was performed for 5 min with the introduction of ethylene at 1.0 atm. 2 ml of a hydrochloric acid-ethanol solution (v/v, 1:10) was added to terminate the polymerization reaction. The polymerization reaction liquid was further poured into 300 ml of ethanol for settling, and vacuum drying was performed at 60° C. for 24 h to obtain an ethylene-1-octene polymer with a net weight of 2.06 g.

Example 45

An ethylene-1-octene copolymer was prepared according to the method of Example 44, except that the input amount of 1-octene was changed to 40 mmol.

Example 46

An ethylene-1-octene copolymer was prepared according to the method of Example 44, except that the input amount of 1-octene was changed to 10 mmol.

Example 47

An ethylene-1-octene copolymer was prepared according to the method of Example 44, except that the metallocene complex I-2 was replaced by the metallocene complex I-6 obtained in Example 4.

Example 48

An ethylene-1-octene copolymer was prepared according to the method of Example 44, except that the metallocene complex I-2 was replaced by the metallocene complex I-10 obtained in Example 5.

Example 49

An ethylene-1-octene copolymer was prepared according to the method of Example 44, except that the metallocene complex I-2 was replaced by the metallocene complex I-13 obtained in Example 7.

Example 50

An ethylene-1-octene copolymer was prepared according to the method of Example 44, except that the metallocene complex I-2 was replaced by the metallocene complex I-18 obtained in Example 10.

Example 51

An ethylene-1-octene copolymer was prepared according to the method of Example 44, except that the metallocene complex I-2 was replaced by the metallocene complex I-21 obtained in Example 12.

The ethylene-1-octene copolymers obtained in Examples 44-51 were detected, and the number average molecular weight $M_n$ and the molecular weight distribution ($M_w/M_n$) were all determined by GPC (polystyrene was used as a reference material) and their performance detection results were obtained and can be seen in Table 5. The dry polymer was determined for the content of 1-octene using a carbon nuclear magnetic resonance spectrogram (the calculation method can be seen in J. C. Randall, *JMS Rev. Macromol. Chem. Phys.* C29, 1989, 201).

TABLE 5

Ethylene/1-octene copolymerization results

|  | Metallocene complex | Ethylene (atm) | 1-octene (mmol) | Yield (g) | Activity ($10^6$ g/mol · Ln · h) | 1-octene content (mol %) | $M_n^b$ (×$10^4$) | $M_w/M_n$ |
|---|---|---|---|---|---|---|---|---|
| Example 44 | I-2 | 1 | 20 | 2.06 | 2.5 | 23 | 2.06 | 1.9 |
| Example 45 | I-2 | 1 | 40 | 1.41 | 1.7 | 29 | 1.94 | 2.1 |
| Example 46 | I-2 | 1 | 10 | 0.69 | 0.8 | 18 | 2.68 | 1.5 |
| Example 47 | I-6 | 1 | 20 | — | — | — | — | — |
| Example 48 | I-10 | 1 | 20 | 1.11 | 1.3 | 16 | 2.11 | 1.8 |
| Example 49 | I-13 | 1 | 20 | 0.89 | 1.1 | 19 | 3.21 | 1.7 |
| Example 50 | I-18 | 1 | 20 | — | — | — | — | — |
| Example 51 | I-21 | 1 | 20 | — | — | — | — | — |

Example 52

In a glove box, 30 ml of toluene and 0.40 g (5 mmol) of 1,3-cyclohexadiene were added to a 100 ml two-necked flask and were mixed with stirring. This flask was taken out of the glove box and was connected to a Schlenk line. The temperature of the flask was maintained at 40° C. by an oil bath, and then saturated with ethylene (1 atm) for three times under vigorous stirring. 36.8 mg (40 µmol) of [Ph$_3$C][B(C$_6$F$_5$)$_4$], 18.4 mg (40 µmol) of the metallocene complex I-3 obtained in Example 3, 0.4 ml of Al($^i$Bu)$_3$ (0.5 mol/L), and toluene were mixed and were stirred for 1 min to prepare an activated catalyst composition. The catalyst composition was rapidly injected into the flask by a syringe to initiate polymerization, the polymerization reaction was performed for 5 min with the introduction of ethylene at 1.0 atm. 2 ml of a hydrochloric acid-ethanol solution (v/v, 1:10) was added to terminate the polymerization reaction. The polymerization reaction liquid was further poured into 300 ml of ethanol for settling, and vacuum drying was performed at 40° C. for 24 h to obtain an ethylene-1,3-cyclohexadiene polymer with a net weight of 1.24 g.

Example 53

An ethylene-1,3-cyclohexadiene polymer was prepared according to the method of Example 52, except that the input amount of 1,3-cyclohexadiene was changed to 10 mmol.

Example 54

An ethylene-1,3-cyclohexadiene polymer was prepared according to the method of Example 52, except that the metallocene complex I-3 was replaced by the metallocene complex I-10 obtained in Example 5.

Example 55

An ethylene-1,3-cyclohexadiene polymer was prepared according to the method of Example 52, except that the metallocene complex I-3 was replaced by the metallocene complex I-16 obtained in Example 9.

Example 56

An ethylene-1,3-cyclohexadiene polymer was prepared according to the method of Example 52, except that the metallocene complex I-3 was replaced by the metallocene complex I-19 obtained in Example 11.

The ethylene-1,3-cyclohexadiene polymers obtained in Examples 52-56 were detected, and the number average molecular weight $M_n$ and the molecular weight distribution ($M_w/M_n$) were all determined by GPC (polystyrene was used as a reference material) and their performance detection results were obtained and can be seen in Table 6. The dry polymer was determined for the content of 1,3-cyclohexadiene using a hydrogen nuclear magnetic resonance spectrogram (the calculation method can be seen in R. Maromol. Chem. Phys. 2005, 206, 195).

TABLE 6

Ethylene/1,3-cyclohexadiene copolymerization results

|  | Metallocene complex | 1,3-cyclohexadiene (mmol) | Yield (g) | Activity ($10^6$ g/mol · Sc · h) | 1,3-cyclohexadiene content (mol %) | $M_n^b$ (×$10^4$) | $M_w/M_n$ |
|---|---|---|---|---|---|---|---|
| Example 52 | I-3 | 5 | 1.24 | 0.37 | 8 | 3.2 | 2.1 |
| Example 53 | I-3 | 10 | 0.34 | 0.10 | 37 | 2.5 | 1.8 |
| Example 54 | I-10 | 5 | 0.95 | 0.29 | 9 | 3.8 | 1.7 |
| Example 55 | I-16 | 5 | 0.87 | 0.26 | 7 | 10.2 | 2.4 |
| Example 56 | I-19 | 5 | 0.63 | 0.19 | 8 | 7.6 | 1.9 |

Example 57

In a glove box, 30 ml of toluene, 2.64 g (20 mmol) of DCPD, and 1.88 g (20 mmol) of NB were added to a 100 ml two-necked flask and were mixed with stirring. This flask was taken out of the glove box and was connected to a Schlenk line. The temperature of the flask was maintained at 40° C. by an oil bath, and then saturated with ethylene (1 atm) for three times under vigorous stirring. 9.2 mg (10 µmol) of [Ph$_3$C][B(C$_6$F$_5$)$_4$], 4.8 mg (10 µmol) of the metallocene complex I-2 obtained in Example 2, 0.1 ml of Al($^i$Bu)$_3$ (0.5 mol/L), and toluene were mixed and were stirred for 1 min to prepare an activated catalyst composition. The catalyst composition was rapidly injected into the flask by a syringe to initiate polymerization. The polymerization reaction was performed for 5 min with the introduction of ethylene at 1.0 atm. 2 ml of a hydrochloric acid-ethanol solution (v/v, 1:10) was added to terminate the polymerization reaction. The polymerization reaction liquid was further poured into 300 ml of ethanol for settling, and vacuum drying was performed at 40° C. for 36 h to obtain an ethylene-DCPD-NB polymer with a net weight of 2.08 g.

Figure 5:
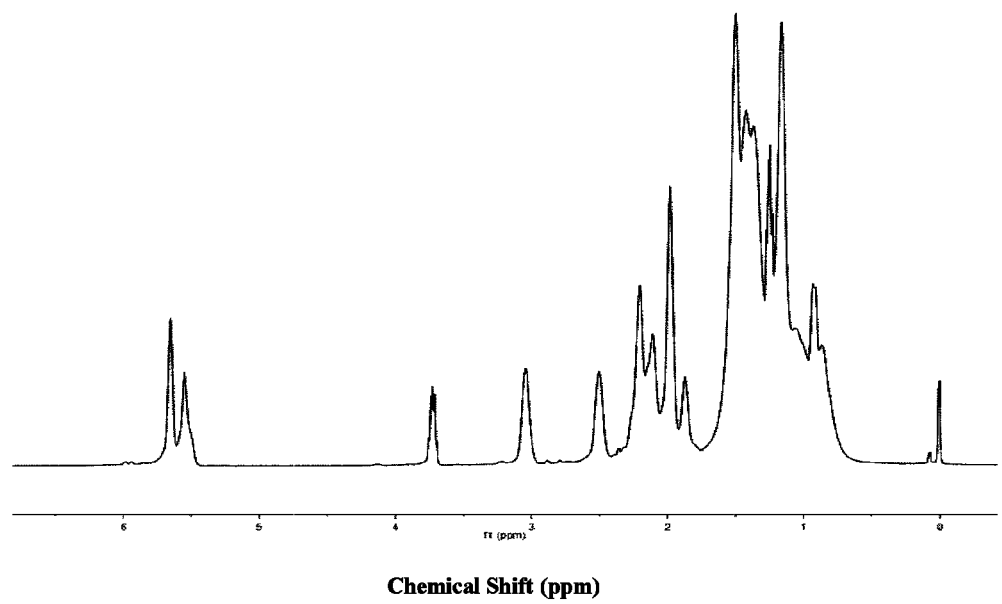
FIG. 5 is a hydrogen nuclear magnetic resonance spectrogram of an ethylene-NB-DCPD polymer obtained in Example 57 of this invention.

The ethylene-DCPD-NB polymer obtained in Example 57 was analyzed using nuclear magnetic resonance to obtain a hydrogen nuclear magnetic resonance spectrogram thereof as shown in FIG. 5.

Example 58

An ethylene-DCPD-NB polymer was prepared according to the method of Example 57, except that the input amount of NB was changed to 10 mmol to obtain a polymer with a net weight of 1.86 g.

The ethylene-DCPD-NB polymers obtained in Examples 57-58 were detected, and the number average molecular weight $M_n$ and the molecular weight distribution ($M_w/M_n$) were all determined by GPC (polystyrene was used as a reference material); the glass transition temperature and the melting point were determined by DSC method; and their performance detection results were obtained and can be seen in Table 7. The dry polymer was determined for the contents of DCPD and NB using a hydrogen nuclear magnetic resonance spectrogram (the calculation method can be seen in US 2008/0221275 A1).

TABLE 7

Ethylene/DCPD/NB copolymerization results

|  | DCPD (mmol) | NB (mmol) | Activity (10$^6$ g/mo · lSc · h) | DCPD content (mol %) | NB content (mol %) | $M_n^b$ (×10$^4$) | $M_w/M_n$ | $T_g^c$ (° C.) |
|---|---|---|---|---|---|---|---|---|
| Example 57 | 20 | 20 | 2.5 | 19 | 31 | 1.74 | 1.56 | 168 |
| Example 58 | 20 | 10 | 2.2 | 23 | 25 | 2.11 | 1.62 | 152 |

Those described above are merely preferred embodiments of this invention, and it is to be indicated that, with respect to the ordinary person skilled in the art, various improvements and modifications can also be made without departing from the principle of this invention. These improvements and modifications should be considered as the scope protected by this invention.

What is claimed is:

1. A metallocene complex represented by formula (I):

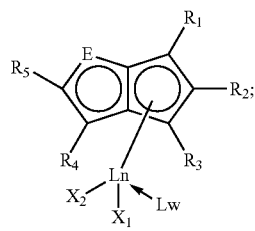

(I)

wherein Ln is one of scandium (Sc), yttrium (Y) and the fifteen elements of lanthanides having an atomic number of 57-71;

R$_1$, R$_2$, R$_3$, R$_4$, and R$_5$ are each independently selected from H, C1-C20 alkyl group, C1-C20 alkyl group containing acetal group, C1-C20 alkyl group containing ketal group, C1-C20 alkyl group containing ether group, C1-C20 alkenyl group, C1-C20 alkenyl group containing acetal group, C1-C20 alkenyl group containing ketal group, C1-C20 alkenyl group containing ether group, C6-C20 aryl group, C6-C20 aryl group containing acetal group, C6-C20 aryl group containing ketal group, C6-C20 aryl group containing ether group, C1-C20 silyl group, C1-C20 silyl group containing acetal group, C1-C20 silyl group containing ketal group, and C1-C20 silyl group containing ether group, or R$_1$ and R$_2$ are linked to each other to form a ring, or R$_2$ and R$_3$ are linked to each other to form a ring, or R$_4$ and R$_5$ are linked to each other to form a ring;

E is O, S or N—R; R is methyl group, benzene ring, or substituted benzene ring;

X$_1$ and X$_2$ are each independently selected from hydrogen, C1-C20 aliphatic group, C1-C20 alicyclic group, phenyl group, substituted phenyl group, C1-C20 alkoxy group, C1-C20 alkylamino group, C1-C20 arylamino group, C1-C20 silyl group, allyl group, allyl derivative, borohydride group, and halogen atom; said substituted phenyl group is phenyl group substituted by one or more of C1-C20 aliphatic group, C1-C20 alicyclic group, and aromatic group; and L is a neutral Lewis base, and w is an integer of 0-3.

2. The metallocene complex according to claim 1, wherein the C1-C20 aliphatic group is selected from methyl group, ethyl group, propyl group, isopropyl group, butyl group, sec-butyl group, or tert-butyl group.

3. The metallocene complex according to claim 1, wherein the X$_1$ and X$_2$ are each independently selected from silylamino group, dimethylamino group, diethylamino group, dipropylamino group, N,N-dimethylaminophenyl group, trimethylsilylmethyl group, bis(trimethylsilyl)methyl group, o-methylthiophenyl group, o-dimethylphosphinophenyl group, tetrahydroboryl group, methoxy group, ethoxy group, isopropoxy group, n-propoxy group, or n-butoxy group.

4. The metallocene complex according to claim 1, wherein the allyl derivative is —C$_3$H$_n$ (R$_6$); said n is 4; said R$_6$ is C1-C20 aliphatic group, C1-C20 alicyclic group, phenyl group, or substituted phenyl group wherein the phenyl group is substituted by one or more of C1-C20 aliphatic group, C1-C20 alicyclic group, and aromatic group.

5. The metallocene complex according to claim 1, wherein the L is tetrahydrofuran, ethyl ether, or toluene.

6. A preparation method of a metallocene complex, comprising:

performing a reaction of a cyclopentadienyl ligand represented by formula (II) and a rare earth compound in a first organic solvent under the protective condition of an inert gas to obtain a metallocene complex represented by formula (I), wherein $X_1$ and $X_2$ are each independently —$CH_2Si(CH_3)_3$; said rare earth compound contains groups $X_1$ and $X_2$;

or, performing a first reaction of a cyclopentadienyl ligand represented by formula (II) and an alkyl lithium in a second organic solvent under the protective condition of an inert gas, then performing a second reaction by adding a rare earth halide, and performing a third reaction by further adding an allyl Grignard reagent and/or an allyl derivative Grignard reagent, to obtain a metallocene complex represented by formula (I) wherein $X_1$ and $X_2$ are each independently an allyl group or an allyl derivative;

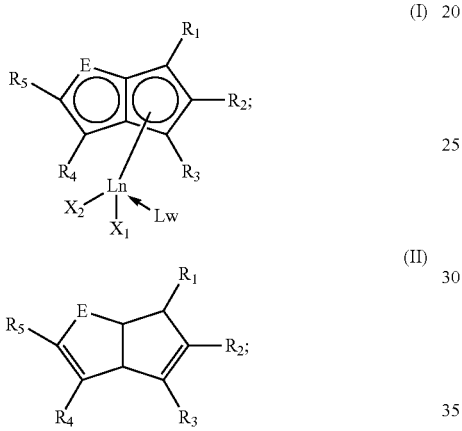

wherein Ln is one of scandium (Sc), yttrium (Y) and the fifteen elements of lanthanides having an atomic number of 57-71;

$R_1$, $R_2$, $R_3$, $R_4$, and $R_5$ are each independently selected from H, C1-C20 alkyl group, C1-C20 alkyl group containing acetal group, C1-C20 alkyl group containing ketal group, C1-C20 alkyl group containing ether group, C1-C20 alkenyl group, C1-C20 alkenyl group containing acetal group, C1-C20 alkenyl group containing ketal group, C1-C20 alkenyl group containing ether group, C6-C20 aryl group, C6-C20 aryl group containing acetal group, C6-C20 aryl group containing ketal group, C6-C20 aryl group containing ether group, C1-C20 silyl group, C1-C20 silyl group containing acetal group, C1-C20 silyl group containing ketal group, and C1-C20 silyl group containing ether group, or $R_1$ and $R_2$ are linked to each other to form a ring, or $R_2$ and $R_3$ are linked to each other to form a ring, or $R_4$ and $R_5$ are linked to each other to form a ring;

E is O, S or N—R; R is methyl group, benzene ring, or substituted benzene ring;

$X_1$ and $X_2$ are each independently selected from —$CH_2Si(CH_3)_3$, allyl group, and allyl derivative; and L is a neutral Lewis base, and w is an integer of 0-3.

7. A catalyst composition, comprising a metallocene complex represented by formula (I) and an organic boron salt;

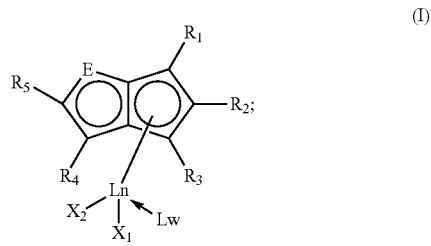

wherein Ln is one of scandium (Sc), yttrium (Y) and the fifteen elements of lanthanides having an atomic number of 57-71;

$R_1$, $R_2$, $R_3$, $R_4$, and $R_5$ are each independently selected from H, C1-C20 alkyl group, C1-C20 alkyl group containing acetal group, C1-C20 alkyl group containing ketal group, C1-C20 alkyl group containing ether group, C1-C20 alkenyl group, C1-C20 alkenyl group containing acetal group, C1-C20 alkenyl group containing ketal group, C1-C20 alkenyl group containing ether group, C6-C20 aryl group, C6-C20 aryl group containing acetal group, C6-C20 aryl group containing ketal group, C6-C20 aryl group containing ether group, C1-C20 silyl group, C1-C20 silyl group containing acetal group, C1-C20 silyl group containing ketal group, and C1-C20 silyl group containing ether group, or $R_1$ and $R_2$ are linked to each other to form a ring, or $R_2$ and $R_3$ are linked to each other to form a ring, or $R_4$ and $R_5$ are linked to each other to form a ring;

E is O, S or N—R; R is methyl group, benzene ring, or substituted benzene ring;

$X_1$ and $X_2$ are each independently selected from hydrogen, C1-C20 aliphatic group, C1-C20 alicyclic group, phenyl group, substituted phenyl group, C1-C20 alkoxy group, C1-C20 alkylamino group, C1-C20 arylamino group, C1-C20 silyl group, allyl group, allyl derivative, borohydride group, and halogen atom; said substituted phenyl group is phenyl group substituted by one or more of C1-C20 aliphatic group, C1-C20 alicyclic group, and aromatic group; and L is a neutral Lewis base, and w is an integer of 0-3.

8. The catalyst composition according to claim 7, further comprising an alkyl aluminum.

9. A preparation method of a polymer, comprising the step of:

mixing the catalyst composition according to claim 7 with an olefin monomer and performing a polymerization reaction to obtain the polymer.

10. The preparation method according to claim 9, wherein the olefin monomer is selected from one or more of styrene, substituted styrene, ethylene, α-olefins, cyclic olefins, and non-conjugated dienes.

* * * * *